United States Patent
Muller

(10) Patent No.: US 10,449,279 B2
(45) Date of Patent: Oct. 22, 2019

(54) GUIDE FEATURES FOR PERCUTANEOUS CATHETER PUMP

(71) Applicant: TC1 LLC, Pleasanton, CA (US)

(72) Inventor: Paul F. Muller, San Carlos, CA (US)

(73) Assignee: TC1 LLC, Pleasanton, CA (US)

( * ) Notice: Subject to any disclaimer, the term of this patent is extended or adjusted under 35 U.S.C. 154(b) by 74 days.

(21) Appl. No.: 15/504,447

(22) PCT Filed: Aug. 14, 2015

(86) PCT No.: PCT/US2015/045370
§ 371 (c)(1),
(2) Date: Feb. 16, 2017

(87) PCT Pub. No.: WO2016/028644
PCT Pub. Date: Feb. 25, 2016

(65) Prior Publication Data
US 2017/0232169 A1    Aug. 17, 2017

Related U.S. Application Data

(60) Provisional application No. 62/038,678, filed on Aug. 18, 2014.

(51) Int. Cl.
*A61M 1/12*   (2006.01)
*A61M 1/10*   (2006.01)
(Continued)

(52) U.S. Cl.
CPC ............ *A61M 1/122* (2014.02); *A61M 1/102* (2014.02); *A61M 1/1008* (2014.02);
(Continued)

(58) Field of Classification Search
CPC .............................. A61M 1/122; A61M 1/125
See application file for complete search history.

(56) References Cited

U.S. PATENT DOCUMENTS 2,789,511 A    4/1957    Doble
3,510,229 A    5/1970    Smith
(Continued)

FOREIGN PATENT DOCUMENTS

CA    2701810 A1    4/2009
EP    0453234 A1    10/1991
(Continued)

OTHER PUBLICATIONS

International Search Report received in International Patent Application No. PCT/US2003/004401, dated Nov. 10, 2003, 7 pages.
(Continued)

*Primary Examiner* — Alyssa M Alter
(74) *Attorney, Agent, or Firm* — Armstrong Teasdale LLP

(57) ABSTRACT

A catheter assembly can include a cannula disposed at a distal portion of the catheter assembly. The cannula can have a collapsed configuration and an expanded configuration. The cannula can be arranged to permit the flow of blood therethrough when in the expanded configuration. The catheter assembly can comprise a tip member coupled with a distal portion of the cannula. A guide feature can be configured to receive a guidewire through a guide lumen formed through the guide feature. The catheter assembly can be configured such that, when the catheter assembly is inserted into a patient with the guidewire, the guidewire passes through the guide lumen and along at least a portion of an outer surface of the catheter assembly.

16 Claims, 25 Drawing Sheets

(51) Int. Cl.
*A61M 25/09* (2006.01)
*A61M 25/00* (2006.01)
*A61M 25/01* (2006.01)

(52) U.S. Cl.
CPC .......... *A61M 1/1036* (2014.02); *A61M 1/125* (2014.02); *A61M 25/09* (2013.01); *A61M 1/101* (2013.01); *A61M 1/1024* (2014.02); *A61M 1/1034* (2014.02); *A61M 2025/0024* (2013.01); *A61M 2025/018* (2013.01); *A61M 2025/0177* (2013.01)

(56) References Cited

U.S. PATENT DOCUMENTS

| | | |
|---|---|---|
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,304,524 A | 12/1981 | Coxon |
| D264,134 S | 4/1982 | Xanthopoulos |
| 4,382,199 A | 5/1983 | Isaacson |
| 4,458,366 A | 7/1984 | MacGregor et al. |
| 4,537,561 A | 8/1985 | Xanthopoulos |
| 4,589,822 A | 5/1986 | Clausen et al. |
| 4,625,712 A | 12/1986 | Wampler |
| 4,673,334 A | 6/1987 | Allington et al. |
| 4,686,982 A | 8/1987 | Nash |
| 4,696,667 A | 9/1987 | Masch |
| 4,704,121 A | 11/1987 | Moise |
| 4,753,221 A | 6/1988 | Kensey et al. |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 5,021,048 A | 6/1991 | Buckholtz |
| 5,044,902 A | 9/1991 | Malbec |
| 5,045,072 A | 9/1991 | Castillo et al. |
| 5,049,134 A | 9/1991 | Golding et al. |
| 5,059,174 A | 10/1991 | Vaillancourt |
| 5,061,256 A | 10/1991 | Wampler |
| 5,089,016 A | 2/1992 | Millner et al. |
| 5,098,256 A | 3/1992 | Smith |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,279,299 A * | 1/1994 | Imran .................... A61N 1/056 600/393 |
| 5,290,227 A | 3/1994 | Pasque |
| 5,300,112 A | 4/1994 | Barr |
| 5,344,443 A | 9/1994 | Palma et al. |
| 5,376,114 A | 12/1994 | Jarvik |
| 5,393,207 A | 2/1995 | Maher et al. |
| 5,405,341 A | 4/1995 | Martin |
| 5,437,541 A | 8/1995 | Vainrub |
| 5,458,459 A | 10/1995 | Hubbard et al. |
| 5,490,763 A | 2/1996 | Abrams et al. |
| 5,527,159 A | 6/1996 | Bozeman, Jr. et al. |
| 5,534,287 A | 7/1996 | Lukic |
| 5,586,868 A | 12/1996 | Lawless et al. |
| 5,613,935 A | 3/1997 | Jarvik |
| 5,725,513 A | 3/1998 | Ju et al. |
| 5,729,299 A | 3/1998 | Suzuki et al. |
| 5,735,897 A | 4/1998 | Buirge |
| 5,741,234 A | 4/1998 | Aboul-Hosn |
| 5,746,709 A | 5/1998 | Rom et al. |
| 5,749,855 A | 5/1998 | Reitan |
| 5,776,161 A | 7/1998 | Globerman |
| 5,779,721 A | 7/1998 | Nash |
| 5,824,070 A | 10/1998 | Jarvik |
| 5,859,482 A | 1/1999 | Crowell et al. |
| 5,868,702 A | 2/1999 | Stevens et al. |
| 5,888,242 A | 3/1999 | Antaki et al. |
| 5,911,685 A | 6/1999 | Siess et al. |
| 5,927,956 A | 7/1999 | Lim et al. |
| 5,941,813 A | 8/1999 | Sievers et al. |
| 5,951,263 A | 9/1999 | Taylor et al. |
| 5,957,941 A | 9/1999 | Ream |
| 5,993,420 A | 11/1999 | Hyman et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,053,705 A | 4/2000 | Schoeb et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,109,895 A | 8/2000 | Ray et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,203,528 B1 | 3/2001 | Deckert et al. |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,454,775 B1 | 9/2002 | Demarais et al. |
| 6,468,298 B1 | 10/2002 | Pelton |
| 6,494,694 B2 | 12/2002 | Lawless et al. |

(56) References Cited

U.S. PATENT DOCUMENTS

| | | |
|---|---|---|
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | DeBlanc et al. |
| 6,565,598 B1 | 5/2003 | Lootz |
| 6,572,349 B2 | 6/2003 | Sorensen et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,789 B2 | 9/2004 | Siess et al. |
| 6,817,836 B2 | 11/2004 | Nose et al. |
| 6,835,049 B2 | 12/2004 | Ray |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,926,662 B1 | 8/2005 | Aboul-Hosn et al. |
| 6,935,344 B1 | 8/2005 | Aboul-Hosn et al. |
| 6,949,066 B2 | 9/2005 | Bearnson et al. |
| 6,962,488 B2 | 11/2005 | Davis et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B1 | 4/2006 | Aboul-Hosn et al. |
| 7,122,019 B1 | 10/2006 | Kesten et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,238,010 B2 | 7/2007 | Hershberger et al. |
| 7,241,257 B1 | 7/2007 | Ainsworth et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,381,179 B2 | 6/2008 | Aboul-Hosn et al. |
| 7,478,999 B2 | 1/2009 | Limoges |
| 7,491,163 B2 | 2/2009 | Viole et al. |
| 7,534,258 B2 | 5/2009 | Gomez et al. |
| 7,633,193 B2 | 12/2009 | Masoudipour et al. |
| 7,682,673 B2 | 3/2010 | Houston et al. |
| 7,722,568 B2 | 5/2010 | Lenker et al. |
| 7,736,296 B2 | 6/2010 | Siess et al. |
| 7,780,628 B1 | 8/2010 | Keren et al. |
| 7,878,967 B1 | 2/2011 | Khanal |
| 7,934,912 B2 | 5/2011 | Voltenburg, Jr. et al. |
| 7,942,844 B2 | 5/2011 | Moberg et al. |
| 7,998,190 B2 | 8/2011 | Gharib et al. |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,206,350 B2 | 6/2012 | Mann et al. |
| 8,216,122 B2 | 7/2012 | Kung et al. |
| 8,236,040 B2 | 8/2012 | Mayberry et al. |
| 8,277,470 B2 | 10/2012 | Demarais et al. |
| 8,317,715 B2 | 11/2012 | Belleville et al. |
| 8,333,687 B2 | 12/2012 | Farnan et al. |
| 8,364,278 B2 | 1/2013 | Pianca et al. |
| 8,608,635 B2 | 12/2013 | Yomtov et al. |
| 8,690,749 B1 | 4/2014 | Nunez |
| 8,721,517 B2 | 5/2014 | Zeng et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,814,776 B2 | 8/2014 | Hastie et al. |
| 8,944,748 B2 | 2/2015 | Liebing |
| 8,992,406 B2 | 3/2015 | Corbett |
| 9,089,670 B2 | 7/2015 | Scheckel |
| 9,217,442 B2 | 12/2015 | Wiessler et al. |
| 9,314,558 B2 | 4/2016 | Er |
| 9,328,741 B2 | 5/2016 | Liebing |
| 9,358,330 B2 | 6/2016 | Schumacher |
| 2002/0010487 A1 | 1/2002 | Evans et al. |
| 2002/0047435 A1 | 4/2002 | Takahashi et al. |
| 2002/0094287 A1 | 7/2002 | Davis |
| 2002/0107506 A1 | 8/2002 | McGuckin et al. |
| 2002/0111663 A1 | 8/2002 | Dahl et al. |
| 2002/0151761 A1 | 10/2002 | Viole et al. |
| 2003/0018380 A1 | 1/2003 | Craig et al. |
| 2003/0023201 A1 | 1/2003 | Aboul-Hosn et al. |
| 2003/0100816 A1 | 5/2003 | Siess |
| 2003/0135086 A1 | 7/2003 | Khaw et al. |
| 2003/0187322 A1 | 10/2003 | Siess |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0010229 A1 | 1/2004 | Houde et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0116862 A1 | 6/2004 | Ray |
| 2004/0152944 A1 | 8/2004 | Medvedev et al. |
| 2004/0253129 A1 | 12/2004 | Sorensen et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0137680 A1 | 6/2005 | Ortiz et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0008349 A1 | 1/2006 | Khaw |
| 2006/0036127 A1 | 2/2006 | Delgado, III et al. |
| 2006/0058869 A1 | 3/2006 | Olson et al. |
| 2006/0062672 A1 | 3/2006 | McBride et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2007/0142785 A1 | 6/2007 | Lundgaard et al. |
| 2007/0156006 A1 | 7/2007 | Smith et al. |
| 2007/0203442 A1 | 8/2007 | Bechert et al. |
| 2007/0212240 A1 | 9/2007 | Voyeux et al. |
| 2007/0217932 A1 | 9/2007 | Voyeux et al. |
| 2007/0217933 A1 | 9/2007 | Haser et al. |
| 2007/0233270 A1 | 10/2007 | Weber et al. |
| 2007/0237739 A1 | 10/2007 | Doty |
| 2007/0248477 A1 | 10/2007 | Nazarifar et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103516 A1 | 5/2008 | Wulfman et al. |

(56) References Cited

U.S. PATENT DOCUMENTS

| | | |
|---|---|---|
| 2008/0103591 A1 | 5/2008 | Siess |
| 2008/0114339 A1 | 5/2008 | McBride et al. |
| 2008/0119943 A1 | 5/2008 | Armstrong |
| 2008/0132748 A1 | 6/2008 | Shifflette |
| 2008/0167679 A1 | 7/2008 | Papp |
| 2008/0306327 A1 | 12/2008 | Shifflette |
| 2009/0018498 A1 | 1/2009 | Chiu et al. |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0053085 A1 | 2/2009 | Thompson et al. |
| 2009/0062597 A1 | 3/2009 | Shifflette |
| 2009/0073037 A1 | 3/2009 | Penna et al. |
| 2009/0087325 A1 | 4/2009 | Voltenburg, Jr. et al. |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0030161 A1 | 2/2010 | Duffy |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0191035 A1 | 7/2010 | Kang et al. |
| 2010/0197994 A1 | 8/2010 | Mehmanesh |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1 | 1/2011 | Campbell et al. |
| 2011/0004291 A1 | 1/2011 | Davis et al. |
| 2011/0009687 A1 | 1/2011 | Mohl |
| 2011/0015610 A1 | 1/2011 | Plahey et al. |
| 2011/0034874 A1 | 2/2011 | Reitan et al. |
| 2011/0076439 A1 | 3/2011 | Zeilon |
| 2011/0098805 A1 | 4/2011 | Dwork et al. |
| 2011/0106004 A1 | 5/2011 | Eubanks et al. |
| 2011/0152831 A1 | 6/2011 | Rotem et al. |
| 2011/0152906 A1 | 6/2011 | Escudero et al. |
| 2011/0152907 A1 | 6/2011 | Escudero et al. |
| 2011/0218516 A1 | 9/2011 | Grigorov |
| 2011/0237863 A1 | 9/2011 | Ricci et al. |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2011/0300010 A1 | 12/2011 | Jarnagin et al. |
| 2012/0059213 A1 | 3/2012 | Spence et al. |
| 2012/0059460 A1 | 3/2012 | Reitan |
| 2012/0083740 A1 | 4/2012 | Chebator et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0220854 A1 | 8/2012 | Messerly et al. |
| 2012/0224970 A1 | 9/2012 | Schumacher et al. |
| 2012/0234411 A1 | 9/2012 | Scheckel et al. |
| 2012/0237357 A1 | 9/2012 | Schumacher et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0106212 A1 | 5/2013 | Nakazumi et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0245360 A1 | 9/2013 | Schumacher et al. |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2014/0010686 A1 | 1/2014 | Tanner et al. |
| 2014/0012065 A1 | 1/2014 | Fitzgerald et al. |
| 2014/0039465 A1 | 2/2014 | Schulz et al. |
| 2014/0051908 A1 | 2/2014 | Khanal et al. |
| 2014/0067057 A1 | 3/2014 | Callaway et al. |
| 2014/0088455 A1 | 3/2014 | Christensen et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0303596 A1 | 10/2014 | Schumacher et al. |
| 2015/0031936 A1 | 1/2015 | Larose et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0250399 A1 | 9/2016 | Tiller et al. |
| 2016/0250400 A1 | 9/2016 | Schumacher |
| 2016/0256620 A1 | 9/2016 | Scheckel et al. |

FOREIGN PATENT DOCUMENTS

| | | |
|---|---|---|
| EP | 0533432 A1 | 3/1993 |
| EP | 1393762 A1 | 3/2004 |
| EP | 1591079 A1 | 11/2005 |
| EP | 2298374 A1 | 3/2011 |
| FR | 2267800 A1 | 11/1975 |
| GB | 2239675 A | 7/1991 |
| JP | S4823295 U | 3/1973 |
| JP | S58190448 A | 11/1983 |
| JP | H02211169 A | 8/1990 |
| JP | H06114101 A | 4/1994 |
| JP | H08196624 A | 8/1996 |
| JP | H1099447 A | 4/1998 |
| JP | 3208454 B2 | 9/2001 |
| TW | 500877 B2 | 9/2002 |
| WO | 9526695 A2 | 10/1995 |
| WO | 9715228 A1 | 5/1997 |
| WO | 0019097 A1 | 4/2000 |
| WO | 0043062 A1 | 7/2000 |
| WO | 0069489 A1 | 11/2000 |
| WO | 0117581 A2 | 3/2001 |
| WO | 0124867 A1 | 4/2001 |
| WO | 02070039 A2 | 9/2002 |
| WO | 03103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2010133567 A1 | 11/2010 |
| WO | 2010149393 A1 | 12/2010 |
| WO | 2011035926 A1 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 2012007140 A1 | 1/2012 |
| WO | 2012007141 A1 | 1/2012 |
| WO | 2013148697 A1 | 10/2013 |

(56) References Cited

FOREIGN PATENT DOCUMENTS

| WO | 2013160407 A1 | 10/2013 |
|---|---|---|
| WO | 2014019274 A1 | 2/2014 |
| WO | 2015063277 A2 | 5/2015 |

OTHER PUBLICATIONS

International Search Report received in International Patent Application No. PCT/US2003/004853, dated Nov. 10, 2003, 5 pages.
International Search Report and Written Opinion received in International Patent Application No. PCT/US2010/040847, dated Jan. 6, 2011, 15 pages.
International Search Report and Written Opinion received in International Patent Application No. PCT/US2014/020790, dated Oct. 9, 2014, 9 pages .
International Search Report and Written Opinion received in International Patent Application No. PCT/US2016/051553, dated Mar. 23, 2017, 11 pages.
JOMED Reitan Catheter Pump RCP, Percutaneous Circulatory Support, believed to be published prior to Oct. 15, 2003, 10 pages.
JOMED Reitan Catheter Pump RCP, Feb. 18, 2003, 4 pages.
Krishnamani et al., "Emerging Ventricular Assist Devices for Long-Term Cardiac Support," National Review, Cardiology, Feb. 2010, vol. 7, pp. 71-76.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, vol. 21, No. 5, pp. 425-427.
Mihaylov et al., "Evaluation of the Optimal Driving Mode During Left Ventricular Assist with Pulsatile Catheter Pump in Calves," Artificial Organs, 1999, vol. 23, No. 12, pp. 1117-1122.
Minimally Invasive Cardiac Assist JOMED Catheter PumpTM, believed to be published prior to Jun. 16, 1999, 6 pages.
Morgan, "Medical Shape Memory Alloy Applications—The Market and its Products," Materials Science and Engineering, 2004, vol. A 378, pp. 16-23.
Morsink et al., "Numerical Modelling of Blood Flow Behaviour in the Valved Catheter of the PUCA-Pump, a LVAD," The International Journal of Artificial Organs, 1997, vol. 20, No. 5, pp. 277-284.
Nishimura et al, "The Enabler Cannula Pump: A Novel Circulatory Support System," The International Journal of Artificial Organs, 1999, vol. 22, No. 5, pp. 317-323.
Nullity Action against the owner of the German part DE 50 2007 005 015.6 of European patent EP 2 047 872 B1, dated Jul. 13, 2015, 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, vol. 2, No. 2, pp. 168-172.
Rakhorst et al., "In Vitro Evaluation of the Influence of Pulsatile Intraventricular Pumping on Ventricular Pressure Patterns," Artificial Organs, 1994, vol. 18, No. 7, pp. 494-499.
Reitan, Evaluation of a New Percutaneous Cardiac Assist Device, Department of Cardiology, Faculty of Medicine, Lund University, Sweden, 2002, 172 pages.
Reitan et al., "Hemodynamic Effects of a New Percutaneous Circulatory Support Device in a Left Ventricular Failure Model," ASAIO Journal, 2003, vol. 49, pp. 731-736.
Reitan et al., "Hydrodynamic Properties of a New Percutaneous Intra-Aortic Axial Flow Pump," ASAIO Journal 2000, pp. 323-328.
Rothman, "The Reitan Catheter Pump: A New Versatile Approach for Hemodynamic Support", London Chest Hospital Barts & the London NHS Trust, Oct. 22-27, 2006 (TCT 2006: Transcatheter Cardiovascular Therapeutics 18th Annual Scientific Symposium, Final Program), 48 pages.
Schmitz-Rode et al., "An Expandable Percutaneous Catheter Pump for Left Ventricular Support," Journal of the American College of Cardiology, 2005, vol. 45, No. 11, pp. 1856-1861.
Shabari et al., "Improved Hemodynamic,s with a Novel Miniaturized Intra-Aortic Axial Flow Pump in a Porcine Model of Acute Left Ventricular Dysfunction," ASAIO Journal, 2013, vol. 59, pp. 240-245.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, vol. 118, No. 5, pp. 924-929.
Sharony et al., "Right Heart Support During Off-Pump Coronary Artery Surgery—A Multi-Center Study," The Heart Surgery Forum, 2002, vol. 5, No. 1, pp. 13-16.
Sießet al., "Hydraulic refinement of an intraarterial microaxial blood pump", The International Journal of Artificial Organs, 1995, vol. 18, No. 5, pp. 273-285.
Sieß, "Systemanalyse and Entwicklung intravasaler Rotationspumpen zur Herzunterstützung", Helmholtz-Institut fur Blomedixinische Technik an der RWTH Aachen, Jun. 24, 1998, 105 pages.
Sieß et al., "System analysis and development of intravascular rotation pumps for cardiac assist," Dissertation, Shaker Verlag, Aachen, 1999, 39 pages.
Siess et al., "Basic design criteria for rotary blood pumps," H. Masuda, Rotary Blood Pumps, Springer, Japan, 2000, pp. 69-83.
Sieß et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, Blackwell Science, Inc., International Society for Artificial Organs, vol. 25, No. 5, pp. 414-421.
Smith et al., "First-In-Man Study of the Reitan Catheter Pump for Circulatory Support in Patients Undergoing High-Risk Percutaneous Coronary Intervention," Catheterization and Cardiovascular Interventions, 2009, vol. 73, No. 7, pp. 859-865.
Sokolowski et al., "Medical Applications of Shape Memory Polymers," Biomed. Mater. 2007, vol. 2, pp. S23-S27.
"Statistical Analysis and Clinical Experience with the Recover® Pump Systems", Impella CardioSystems GmbH, Sep. 2005, 2 pages.
Stoeckel et al., "Self-Expanding Nitinol Stents—Material and Design Considerations," European Radiology, 2003, 13 pages.
Stolinski et al., "The heart-pump interaction: effects of a microaxial blood pump," International Journal of Artificial Organs, 2002, vol. 25, Issue 11, pp. 1082-1088.
Supplemental European Search Report received from the European Patent Office in EP Application No. EP 05799883 dated Mar. 19, 2010, 4 pages.
Takagaki et al., "A Novel Miniature Ventricular Assist Device for Hemodynamic Support," ASAIO Journal, 2001, vol. 47, pp. 412-416.
Throckmorton et al., "Flexible Impeller Blades in an Axial Flow Pump for Intravascular Cavopulmonary Assistance of the Fontan Physiology," Cardiovascular Engineering and Technology, Dec. 2010, vol. 1, No. 4, pp. 244-255.
Throckmorton et al., "Uniquely shaped cardiovascular stents enhance the pressure generation of intravascular blood pumps," The Journal of Thoracic and Cardiovascular Surgery, Sep. 2012, vol. 133, No. 3, pp. 704-709.
Verkerke et al., "The PUCA Pump: A Left Ventricular Assist Device," Artificial Organs, 1993, vol. 17, No. 5, pp. 365-368.
Verkerke et al., "Numerical Simulation of the PUCA Pump, A Left Ventricular Assist Device, Abstracts of the XIXth ESAO Congress," The International Journal of Artificial Organs, 1992, vol. 15, No. 9, p. 543.
Verkerke et al., "Numerical Simulation of the Pulsating Catheter Pump: A Left Ventricular Assist Device," Artificial Organs, 1999, vol. 23, No. 10, pp. 924-931.
Wampler et al., "The Sternotomy Hemopump, A Second Generation Intraarterial Ventricular Assist Device," ASAIO Journal, 1993, vol. 39, pp. M218-M223.

(56) References Cited

OTHER PUBLICATIONS

Weber et al., "Principles of Impella Cardiac Support," Supplemental to Cardiac Interventions Today, Aug./Sep. 2009, pp. 3-16.
Written Opinion received in International Patent Application No. PCT/US2003/04853, dated Feb. 25, 2004, 5 pages.
Extended EP Search Report, dated Mar. 15, 2018, for related EP patent application No. EP 15833166.0, 7 pages.
Abiomed, "Impella 5.0 with the Impella Console, Circulatory Support System, Instructions for Use & Clinical Reference Manual," Jun. 2010, 122 pages.
Abiomed—Recovering Hearts. Saving Lives., Impella 2.5 System, Instructions for Use, Jul. 2007, 86 pages.
Aboul-Hosn et al., "The Hemopump: Clinical Results and Future Applications", Assisted Circulation 4, 1995, 14 pages.
Barras et al., "Nitinol—Its Use in Vascular Surgery and Other Applications," Eur. J. Vasc. Endovasc. Surg., 2000, vol. 19, pp. 564-569.
Biscarini et al., "Enhanced Nitinol Properties for Biomedical Applications," Recent Patents on Biomedical Engineering, 2008, vol. 1, No. 3, pp. 180-196.
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the Hemopump Temporary Cardiac Assist System, Johnson & Johnson Interventional Systems, 1988, 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, vol. A273, pp. 149-160.
European Search Report received in European Patent Application No. 05799883.3, dated May 10, 2011, 4 pages.
Extended European Search Report received in European Patent Application No. 07753903.9, dated Oct. 8, 2012, 7 pages.
Extended European Search Report received in European Patent Application No. 13790890.1, dated Jan. 7, 2016, 6 pages.
Extended European Search Report received in European Patent Application No. 13791118.6, dated Jan. 7, 2016, 6 pages.
Extended European Search Report received in European Patent Application No. 13813687.4, dated Feb. 24, 2016, 6 pages.
Extended European Search Report received in European Patent Application No. 13813867.2, dated Feb. 26, 2016, 7 pages.
Extended European Search Report received in European Patent Application No. 14779928.2, dated Oct. 7, 2016, 7 pages.
Extended European Search Report received in European Patent Application No. 14764392.8, dated Oct. 27, 2016, 8 pages.
Federal and Drug Administration 510(k) Summary for Predicate Device IMPELLA 2.5 (K112892), prepared Sep. 5, 2012, 6 pages.
Grech, "Percutaneous Coronary Intervention. I: History and Development," BMJ., May 17, 2003, vol. 326, pp. 1080-1082.
Hsu et al., "Review of Recent Patents on Foldable Ventricular Assist Devices," Recent Patents on Biomedical Engineering, 2012, vol. 5, pp. 208-222.
Ide et al., "Evaluation of the Pulsatility of a New Pulsatile Left Ventricular Assist Device the Integrated Cardioassist Catheter in Dogs," J. of Thorac and Cardiovasc Sur, Feb. 1994, vol. 107, No. 2, pp. 569-575.
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, vol. 16, No. 3, pp. 286-290.
Impella CP®—Instructions for Use & Clinical Reference Manual (United States only), Abiomed, Inc., Jul. 2014, www.abiomed.com, 148 pages.
Impella LD® with the Impella® Controller—Circulatory Support System—Instructions for Use & Clinical Reference Manual (United States only), Abiomed, Inc., Sep. 2010, www.abiomed.com, 132 pages.
International Preliminary Examination Report received in International Patent Application No. PCT/US2003/04853, dated Jul. 26, 2004, 5 pages.
International Preliminary Examination Report received in International Patent Application No. PCT/US2003/04401, dated May 18, 2004, 4 pages.
International Preliminary Report on Patentability and Written Opinion of the International Searching Authority received in International Patent Application No. PCT/US2005/033416, dated Mar. 20, 2007, 7 pages.
International Preliminary Report on Patentability and Written Opinion of the International Searching Authority received in International Patent Application No. PCT/US2007/007313, dated Sep. 23, 2008, 6 pages.
International Preliminary Report on Patentability and Written Opinion received in International Patent Application No. PCT/US2014/020878, dated Sep. 15, 2015, 8 pages.
International Search Report and Written Opinion received in International Patent Application No. PCT/US2005/033416, dated Dec. 11, 2006, 8 pages.
International Search Report and Written Opinion received in International Patent Application No. PCT/US2007/007313, dated Mar. 4, 2008, 6 pages.
International Search Report and Written Opinion received in International Patent Application No. PCT/US2012/020382, dated Jul. 31, 2012, 11 pages.
International Search Report and Written Opinion received in International Patent Application No. PCT/US2012/020369, dated Jul. 30, 2012, 10 pages.
International Search Report and Written Opinion received in International Patent Application No. PCT/US2012/020553, dated Aug. 17, 2012, 8 pages.
International Search Report and Written Opinion received in International Patent Application No. PCT/US2012/020383, dated Aug. 17, 2012; 9 pages.
International Search Report and Written Opinion received in International Patent Application No. PCT/US2013/040798, dated Aug. 21, 2013, 16 pages.
International Search Report and Written Opinion received in International Patent Application No. PCT/US2013/040799, dated Aug. 21, 2013, 19 pages.
International Search Report and Written Opinion received in International Patent Application No. PCT/US2013/040809, dated Sep. 2, 2013, 25 pages.
International Search Report and Written Opinion received in International Patent Application No. PCT/US2013/048332, dated Oct. 16, 2013, 14 pages.
International Search Report and Written Opinion received in International Patent Application No. PCT/US2013/048343, dated Oct. 11, 2013, 15 pages.
International Search Report and Written Opinion received in International Patent Application No. PCT/US2014/020878, dated May 7, 2014, 11 pages.
International Search Report and Written Opinion received in International Patent Application No. PCT/US2015/026013, dated Oct. 22, 2015, 8 pages.
International Search Report and Written Opinion received in International Patent Application No. PCT/US2015/026014, dated Oct. 22, 2015, 8 pages.
International Search Report and Written Opinion received in International Patent Application No. PCT/US2015/026025, dated Oct. 22, 2015, 8 pages.
International Search Report and Written Opinion received in International Patent Application No. PCT/US2015/025959, dated Oct. 22, 2015, 9 pages.
International Search Report and Written Opinion received in International Patent Application No. PCT/US2015/025960, dated Oct. 22, 2015, 11 pages.
International Search Report and Written Opinion received in International Patent Application No. PCT/US2015/045370, dated Feb. 25, 2016, 10 pages.

(56) References Cited

OTHER PUBLICATIONS

International Search Report and Written Opinion received in International Patent Application No. PCT/US2016/014371, dated Jul. 28, 2016, 16 pages.
International Search Report and Written Opinion received in International Patent Application No. PCT/US2016/014379, dated Jul. 29, 2016, 17 pages.
International Search Report and Written Opinion received in International Patent Application No. PCT/US2016/014391, dated Jul. 28, 2016, 15 pages.

* cited by examiner

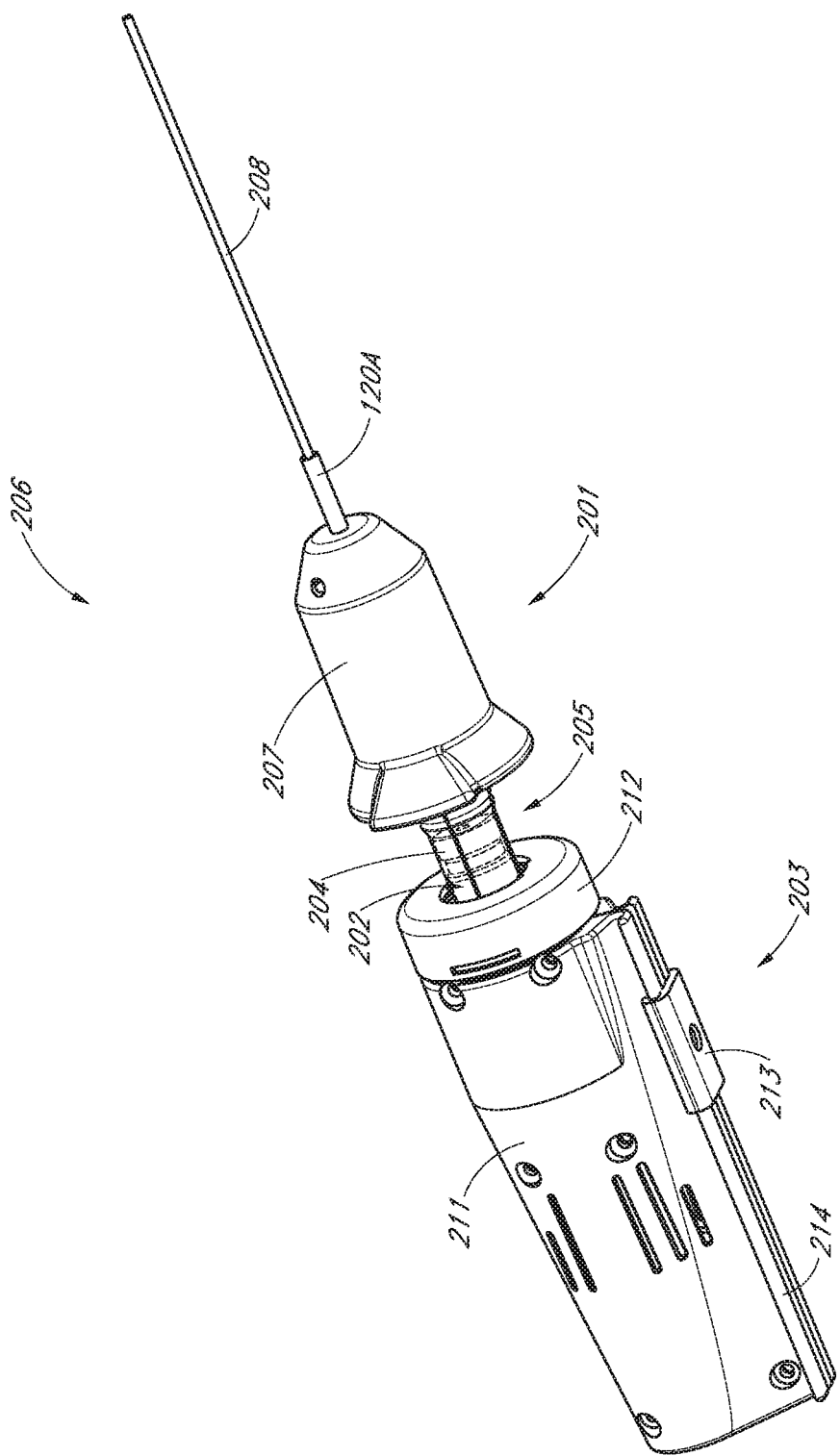

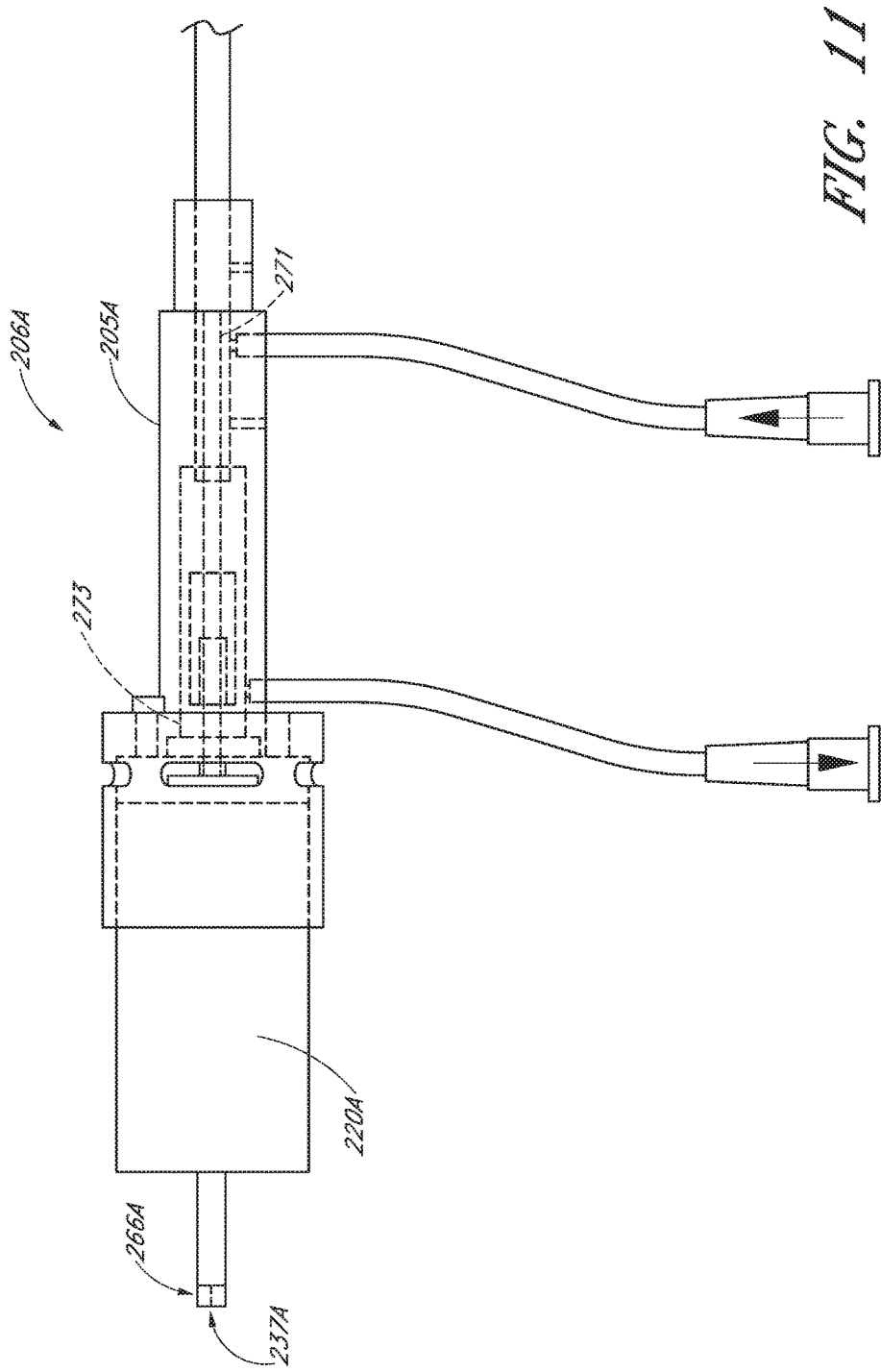

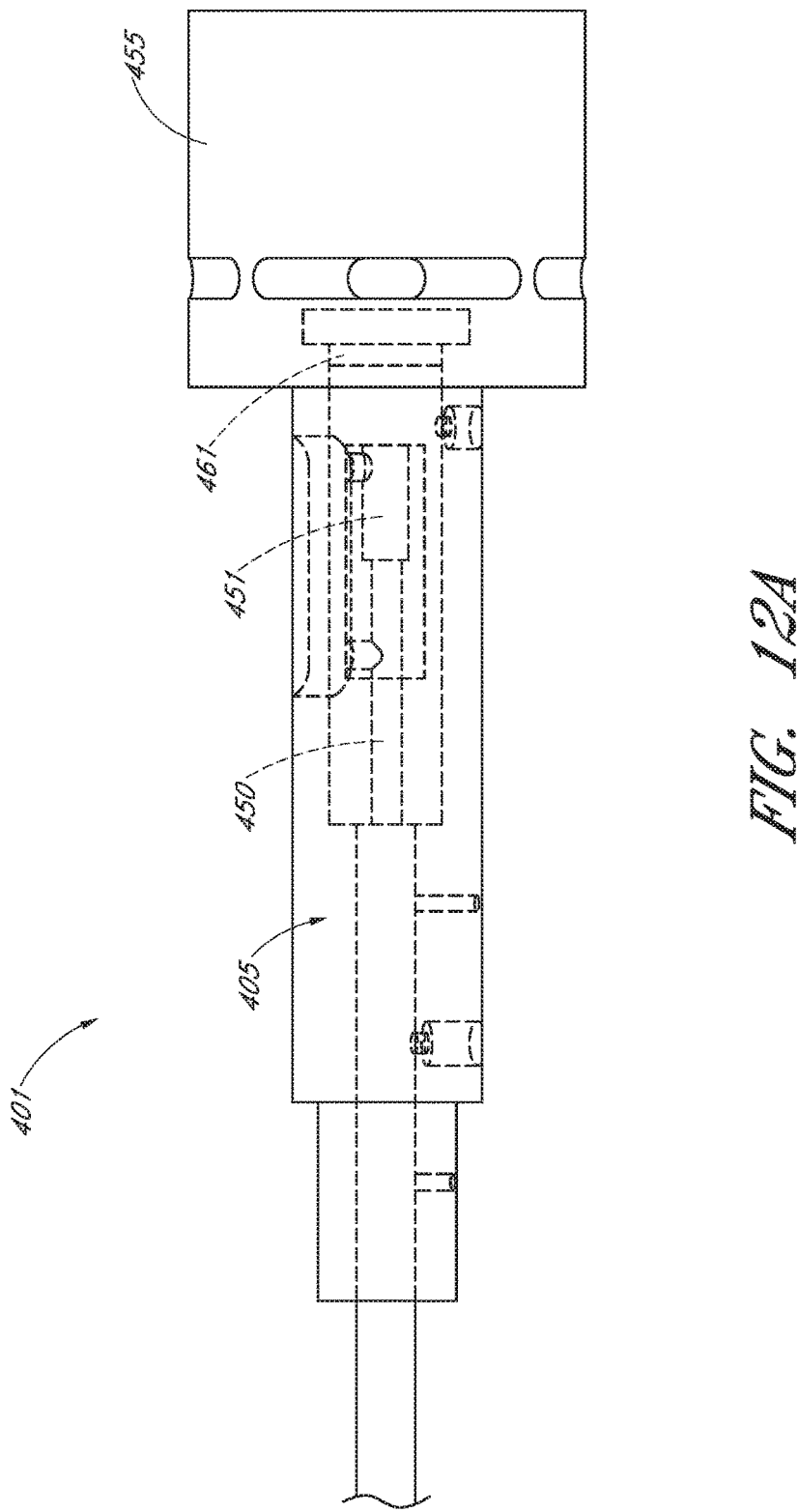

GUIDE FEATURES FOR PERCUTANEOUS CATHETER PUMP

CROSS-REFERENCE TO RELATED APPLICATIONS

This application claims priority to U.S. Provisional Patent Application No. 62/038,678, filed Aug. 18, 2014, the contents of which are incorporated by reference herein in their entirety and for all purposes.

BACKGROUND OF THE INVENTION

Field of the Invention

This application is directed to catheter pumps for mechanical circulatory support of a heart.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e., higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

Further, there is a need for a motor configured to drive an operative device, e.g., a impeller, at a distal portion of the pump. It can be important for the motor to be configured to allow for percutaneous insertion of the pump's operative device.

SUMMARY OF THE INVENTION

There is an urgent need for a pumping device that can be inserted percutaneously and also provide full cardiac rate flows of the left, right, or both the left and right sides of the heart when called for.

In one embodiment, a catheter assembly is disclosed. The catheter assembly can include a cannula disposed at a distal portion of the catheter assembly. The cannula can have a collapsed configuration and an expanded configuration. The cannula can be arranged to permit the flow of blood therethrough when in the expanded configuration. The catheter assembly can comprise a tip member coupled with a distal portion of the cannula. A guide feature can be configured to receive a guidewire through a guide lumen formed through the guide feature. The catheter assembly can be configured such that, when the catheter assembly is inserted into a patient with the guidewire, the guidewire passes through the guide lumen and along at least a portion of an outer surface of the catheter assembly.

In another embodiment, a catheter assembly is disclosed. The catheter assembly can comprise an expandable cannula disposed at a distal portion of the catheter assembly. The expandable cannula can have a collapsed configuration and an expanded configuration. The expandable cannula can be arranged to permit the flow of blood therethrough when in the expanded configuration. The catheter assembly can include a guide feature having a guide lumen extending distally of a proximal end of the guide feature. The proximal end of the guide feature can be located adjacent to or distal of the proximal end of the expandable cannula.

In one embodiment, a catheter pump is disclosed. The catheter pump can include a catheter assembly. The catheter assembly can include a drive shaft having a proximal end and a distal end. An impeller may be coupled with the distal end of the drive shaft. A driven magnet assembly may be coupled with the proximal end of the drive shaft. The driven magnet assembly can include a driven magnet housing having a driven magnet. The catheter pump can further include a drive system. The drive system can include a motor having an output shaft. The drive system can also include a drive magnet assembly coupled with the output shaft. The drive magnet assembly can include a drive magnet housing with a drive magnet disposed therein. A securement device can be configured to secure the driven magnet housing into engagement with the drive magnet housing during operation of the pump.

In another embodiment, a catheter pump is disclosed. The catheter pump can include a catheter assembly. The catheter assembly can comprise a drive shaft having a proximal end and a distal end. An impeller can be coupled with the distal end of the drive shaft. A rotatable magnet can be coupled with the proximal end. The rotatable magnet can be disposed in a driven magnet housing. Furthermore, the catheter pump can include a drive system comprising a plurality of motor windings configured to induce rotation of the rotatable magnet when the driven magnet housing is engaged with the drive system. A locking device can be configured to be engaged by insertion of the driven magnet housing into an opening of the drive system.

In yet another embodiment, a method is disclosed. The method can include inserting a proximal portion of a catheter assembly containing a magnet into a recess of a drive unit. The method can further include engaging a locking device to secure the proximal portion of the catheter assembly to the drive unit.

In another embodiment, a catheter assembly is disclosed. The catheter assembly can include a catheter body having a proximal portion and a distal portion. An operative device can be coupled to the distal portion of the catheter body. A tip member can be coupled to a distal portion of the operative device. The tip member can have a lumen comprising a first section and a second section connected to the first section. An inner diameter of the first section can be larger than an inner diameter of the second section.

In one embodiment, a catheter pump is provided that includes a catheter assembly and a drive system, and a securement device. The catheter assembly includes a drive shaft, an impeller, and a driven assembly. The drive shaft has a proximal end and a distal end. The impeller is coupled with the distal end of the drive shaft. The driven assembly may be coupled with the proximal end of the drive shaft, the driven assembly is disposed in a driven housing. The drive system includes a motor having an output shaft and a drive assembly coupled with the output shaft. The drive assembly includes a drive housing with at least one magnet disposed therein. The securement device is configured to prevent disengagement of the driven housing from the drive housing during operation of the pump.

In one embodiment, a catheter pump is provided that includes a catheter assembly and a drive system, and a damper. The catheter assembly includes a drive shaft, an impeller, and a driven member. The drive shaft has a proximal end and a distal end. The impeller is coupled with the distal end of the drive shaft. The driven member is coupled with the proximal end of the drive shaft. The drive system includes a motor having an output shaft and a drive member coupled with the output shaft.

In one variant, the catheter pump can have a damper disposed between the drive and driven member. The damper can be configured to isolate the drive member or the motor from vibration in the catheter assembly. The damper can be configured to suppress noise at or around the connection between the drive and drive members.

Preferably, the damper is disposed radially around the output shaft, e.g., completely surrounding the output shaft. The damper can be disposed between separable housings of the catheter assembly and drive system, e.g., abutting a distal face of a drive system housing and a proximal face of a driven member housing disposed on the proximal end of the catheter assembly.

This embodiment can be augmented in some embodiments with a disconnectable coupling between the drive and driven members. For example, a securement device can be configured to permit selective disengagement of these components from each other. The securement device can be configured to prevent disengagement of the driven housing from the drive housing during operation of the pump.

Connection of the drive and driven members can be by the mutual attraction of opposing poles of permanent magnets disposed therein. Alternatively, the driven member can be positioned to be acted upon magnetic fields generated in the winding, e.g., using commutation in the windings. In another embodiment, the drive and driven members are coupled using direct mechanical drive, such as with gears, splines or other abutting surfaces.

In another embodiment, a catheter pump is provided that has a catheter assembly, a drive system, and a locking device. The catheter assembly has a drive shaft that has a proximal end and a distal end. An impeller is coupled with the distal end of the drive shaft. A rotatable magnet is coupled with the proximal end of the drive shaft. The rotatable magnet is disposed in a driven magnet housing. The drive system has a plurality of motor windings configured to induce rotation of the rotatable magnet after the driven magnet housing is engaged with the drive system. The locking device is configured to be engaged by insertion of the driven magnet housing into a portion or recess of the drive system.

Rotation can be induced in the rotatable magnet by the mutual attraction of opposing poles of permanent magnets. The rotatable magnet can be an assembly having one or a first plurality of permanent magnets and one or a second plurality of permanent magnets can be mounted on a shaft of the motor having the motor windings. Pairing of opposite poles of two magnets or of the magnets of the first and second pluralities of permanent magnets can induce rotation that can be transferred to the drive shaft. Alternatively, the rotatable magnet can be positioned to be acted upon magnetic fields generated in the winding, e.g., using commutation in the windings.

In another embodiment, a method is provided. A proximal portion of a catheter assembly containing a magnet is inserted into a recess of a drive unit. A locking device is engaged to secure the proximal portion of the catheter assembly to a distal portion of the drive unit.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 4A is an enlarged view of a priming apparatus shown in FIG. 4;

FIG. 5 is a three dimensional (3D) perspective view of a motor assembly as the drive assembly is being coupled to a driven assembly;

FIG. 11 illustrates a side schematic view of a motor assembly according to another embodiment;

FIGS. 12A-12B illustrates side schematic views of a motor assembly according to yet another embodiment;

More detailed descriptions of various embodiments of components for heart pumps useful to treat patients experiencing cardiac stress, including acute heart failure, are set forth below.

DETAILED DESCRIPTION

This application is directed to apparatuses for guiding a distal portion of a catheter assembly (such as an impeller assembly of a catheter pump) to a treatment location in a patient, such as the heart. For example, various embodiments disclosed herein comprise a guide feature configured to receive a guidewire therethrough. The clinician can maneuver the guidewire to the heart through the patient's vasculature and can insert the guidewire through the guide feature. The clinician can advance the distal portion of the catheter assembly over the guide feature to position the distal portion (such as an impeller) in a chamber of the heart.

In some embodiments, the guide feature can comprise a central lumen formed along the length of the catheter assembly. In some embodiments, a guide feature can comprise a tubular segment on an outside surface of an impeller housing, e.g., a cannula disposed about an impeller. In other embodiments, a guide feature can be configured to guide the guidewire from outside the catheter assembly (e.g., from a tube on the outside of the cannula or sheath) to an internal lumen of a distal tip member. In still other embodiments, the guide feature can be configured to guide the guidewire from outside the catheter assembly to within the cannula and the tip member. In some arrangements, the guide feature can comprise a tubular segment on the outside of the sheath. In other arrangements, the guide feature can comprise a tubular segment on the outside of the tip member.

Additional embodiments of this application are directed to apparatuses for inducing motion of a fluid relative to the apparatus. For example, an operative device, such as an impeller, can be coupled at a distal portion of the apparatus. In particular, various disclosed embodiments generally relate to various configurations for a motor adapted to drive an impeller at a distal end of a catheter pump, e.g., a percutaneous heart pump. The disclosed motor assembly may be disposed outside the patient in some embodiments. In other embodiments, the disclosed motor assembly can be miniaturized and sized to be inserted within the body.

Figure 1:
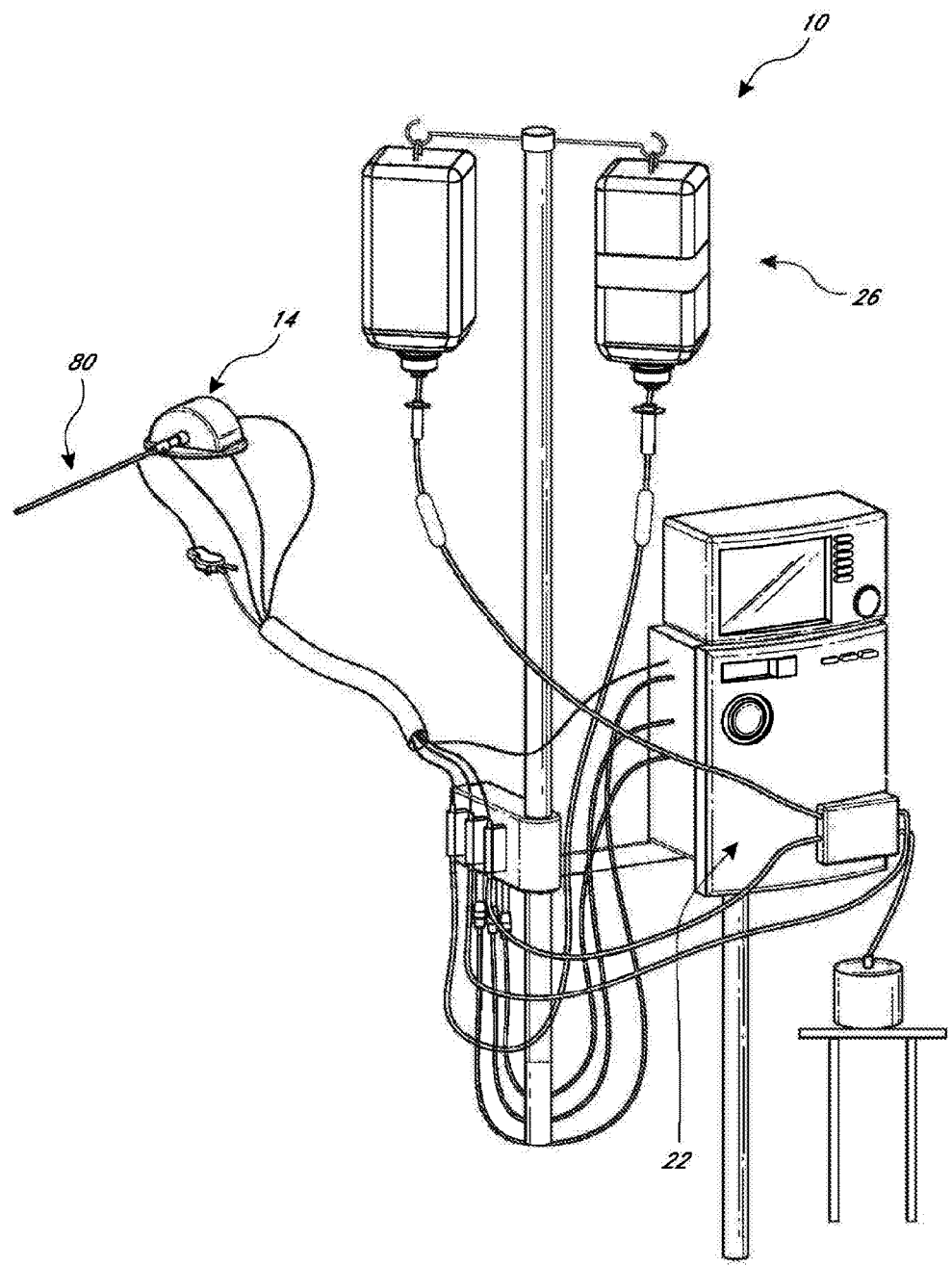
FIG. 1 illustrates one embodiment of a catheter pump configured for percutaneous application and operation.
Figure 2:
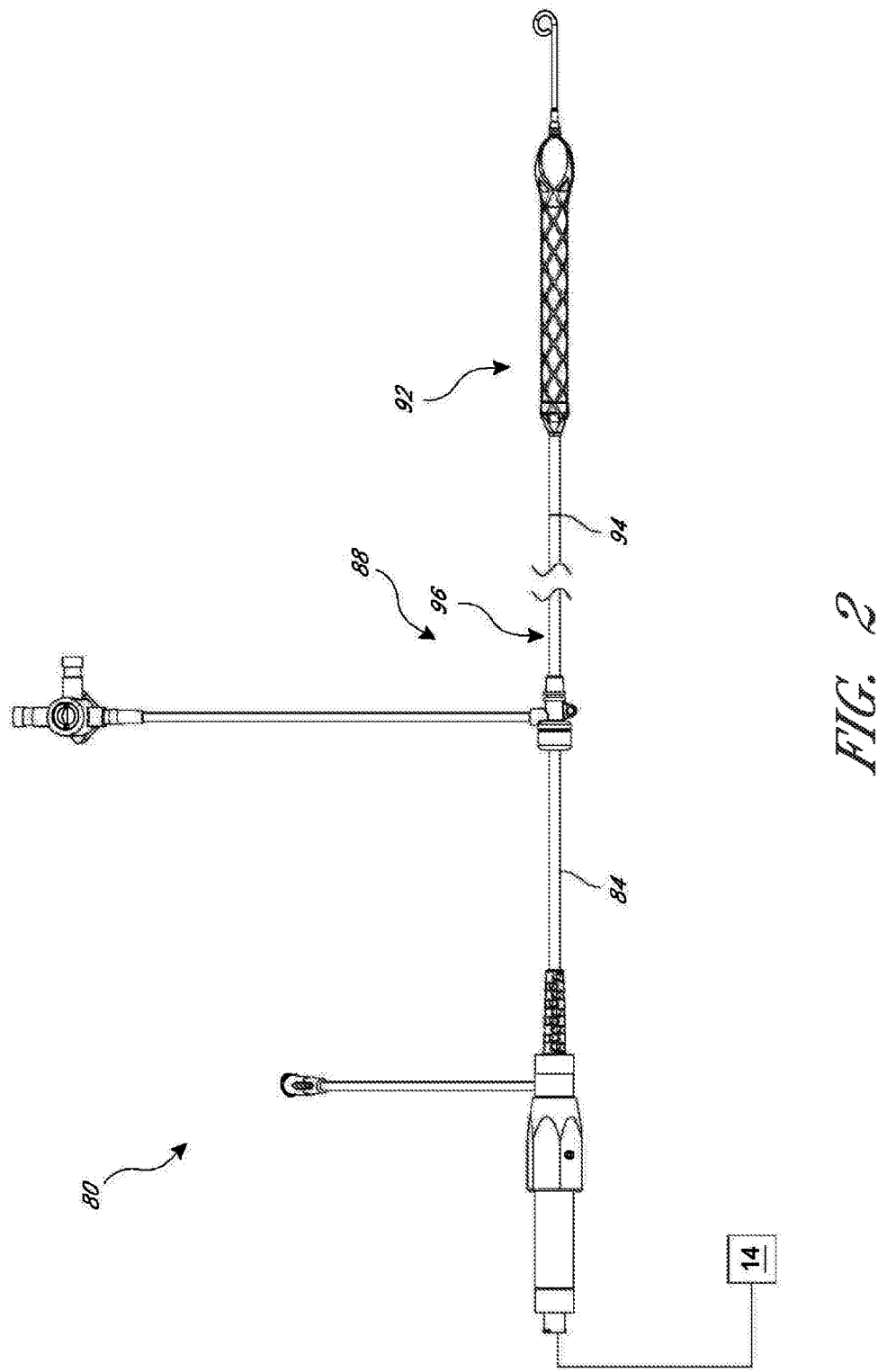
FIG. 2 is a plan view of one embodiment of a catheter adapted to be used with the catheter pump of FIG. 1.
Figure 3:
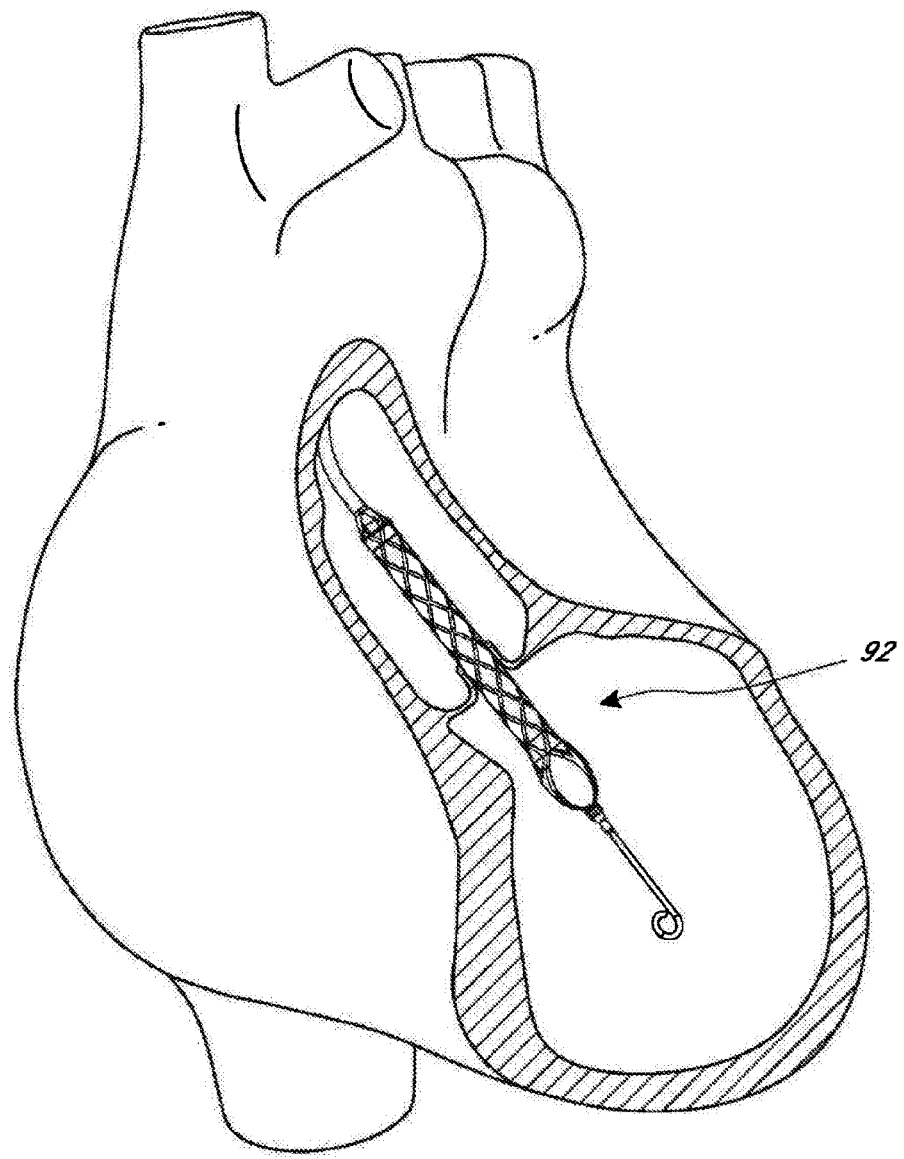
FIG. 3 show a distal portion of the catheter system similar to that of FIG. 2 in position within the anatomy.

FIGS. 1-3 show aspects of a catheter pump 10 that can provide high performance flow rates. The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated remotely by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter. e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes. Various embodiments of a motor are disclosed herein, including embodiments having separate drive and driven assemblies to enable the use of a guidewire guide passing through the catheter pump. As explained herein, a guidewire guide can facilitate passing a guidewire through the catheter pump for percutaneous delivery of the pump's operative device to a patient's heart.

FIG. 3 illustrates one use of the catheter pump 10. A distal portion of the pump 10, which can include an impeller assembly 92, is placed in the left ventricle LV of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. Various guide features are disclosed herein which enable the pump 10 to be advanced over a guidewire to the heart. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat.

Nos. 6,544,216; 7,070,555; and US 2012-0203056A1, all of which are hereby incorporated by reference herein in their entirety for all purposes.

FIG. 2 shows features that facilitate small blood vessel percutaneous delivery and high performance, including up to and in some cases exceeding normal cardiac output in all phases of the cardiac cycle. In particular, the catheter system 80 includes a catheter body 84 and a sheath assembly 88. The impeller assembly 92 is coupled with the distal end of the catheter body 84. The impeller assembly 92 is expandable and collapsible. In the collapsed state, the distal end of the catheter system 80 can be advanced to the heart, for example, through an artery. In the expanded state the impeller assembly 92 is able to pump blood at high flow rates. FIGS. 2 and 3 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example, to a catheter size of about 12.5 FR in various arrangements.

In some embodiments, the impeller assembly 92 includes a self-expanding material that facilitates expansion. The catheter body 84 on the other hand preferably is a polymeric body that has high flexibility. When the impeller assembly 92 is collapsed, as discussed above, high forces are applied to the impeller assembly 92. These forces are concentrated at a connection zone, where the impeller assembly 92 and the catheter body 84 are coupled together. These high forces, if not carefully managed can result in damage to the catheter assembly 80 and in some cases render the impeller within the impeller assembly 92 inoperable. Robust mechanical interface, are provided to assure high performance.

The mechanical components rotatably supporting the impeller within the impeller assembly 92 permit high rotational speeds while controlling heat and particle generation that can come with high speeds. The infusion system 26 delivers a cooling and lubricating solution to the distal portion of the catheter system 80 for these purposes. However, the space for delivery of this fluid is extremely limited. Some of the space is also used for return of the infusate. Providing secure connection and reliable routing of infusate into and out of the catheter assembly 80 is critical and challenging in view of the small profile of the catheter body 84.

When activated, the catheter pump system can effectively increase the flow of blood out of the heart and through the patient's vascular system. In various embodiments disclosed herein, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 62 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following concurrently filed applications: application Ser. No. 13/802,556, entitled "DISTAL BEARING SUPPORT," filed on Mar. 13, 2013; Application No. 61/780,656, entitled "FLUID HANDLING SYSTEM," filed on Mar. 13, 2013; application Ser. No. 13/801,833, entitled "SHEATH SYSTEM FOR CATHETER PUMP," filed on Mar. 13, 2013; application Ser. No. 13/802,570, entitled "IMPELLER FOR CATHETER PUMP," filed on Mar. 13, 2013; and application Ser. No. 13/801,528, entitled "CATHETER PUMP," filed on Mar. 13, 2013.

Figure 4:
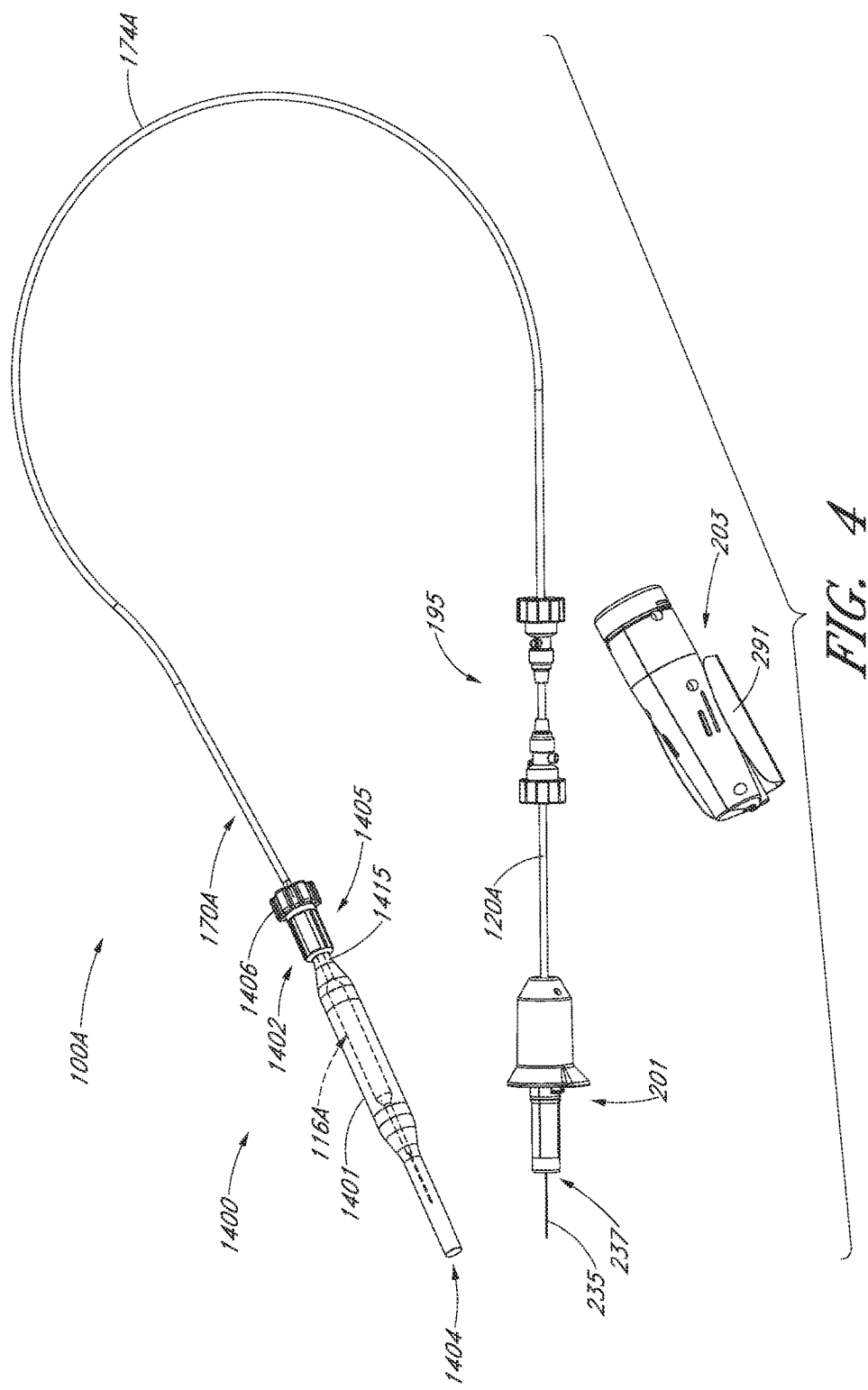
FIG. 4 is a schematic view of a catheter assembly and a drive assembly.
Figure 44:
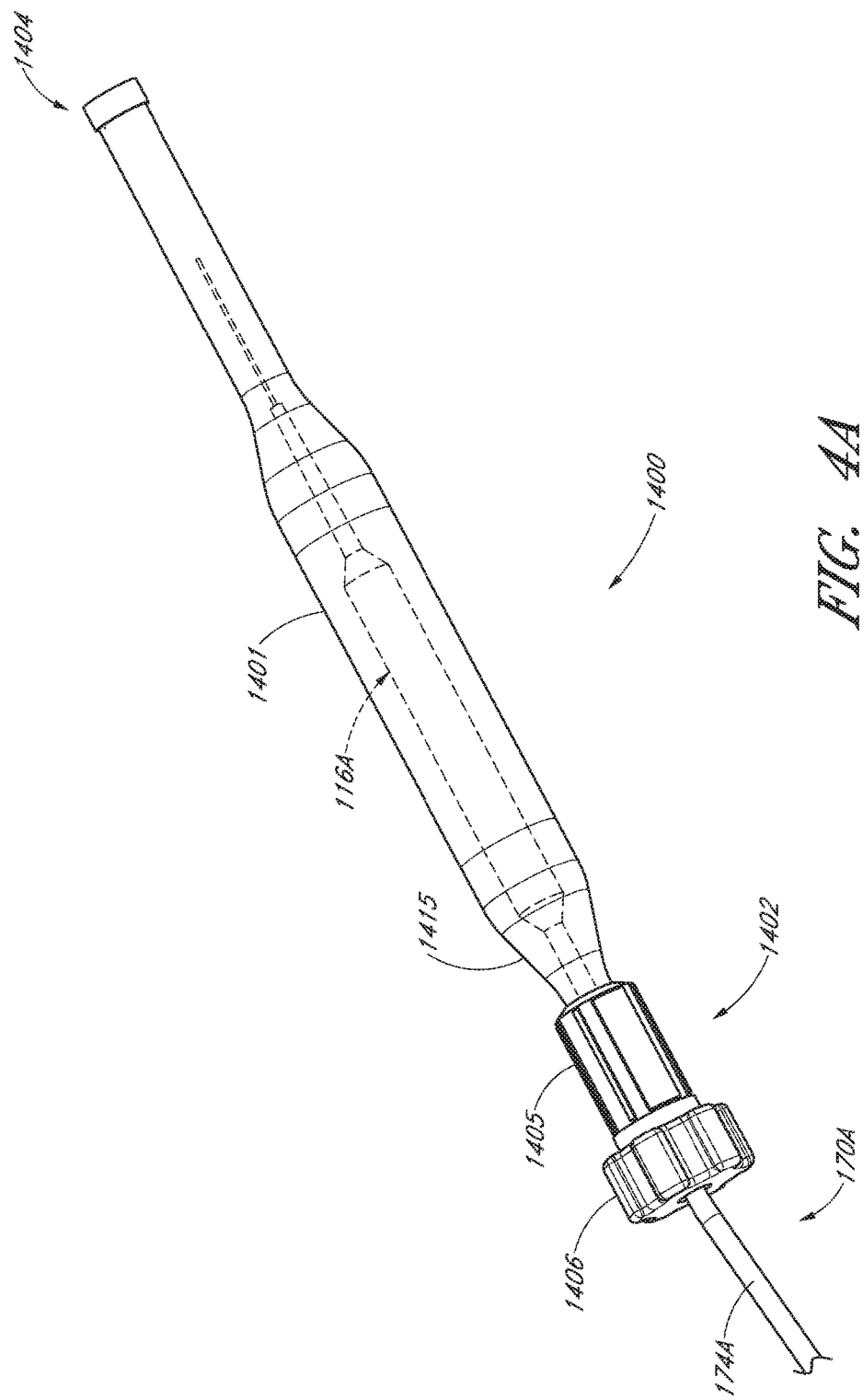

Another example of a catheter assembly 100A is illustrated in FIG. 4. Embodiments of the catheter pump of this application can be configured with a motor that is capable of coupling to (and in some arrangements optionally decoupling from) the catheter assembly 100A. This arrangement provides a number of advantages over a non-disconnectable housing. For example, access can be provided to a proximal end of the catheter assembly 100A prior to or during use. In one configuration, a catheter pump is delivered over a guidewire. In some embodiments, the guidewire may be conveniently extended through the entire length of the catheter assembly 100A and out of a proximal portion thereof that is completely enclosed in a coupled configuration. For this approach, connection of the proximal portion of the catheter assembly 100A to a motor housing can be completed after a guidewire has been used to guide the operative device of the catheter pump to a desired location within the patient, e.g., to a chamber of the patient's heart. In one embodiment, the connection between the motor housing and the catheter assembly is configured to be permanent, such that the catheter assembly, the motor housing and the motor are disposable components. However, in other implementations, the coupling between the motor housing and the catheter assembly is disengageable, such that the motor and motor housing can be decoupled from the catheter assembly after use. In such embodiments, the catheter assembly distal of the motor can be disposable, and the motor and motor housing can be re-usable. In other embodiments, as explained in more detail below, a guidewire can be inserted through other types of guide features to guide the pump to the heart. For example, in other embodiments, there may be no central lumen extending from the proximal end to the distal end of the catheter assembly. Rather the guidewire can be inserted along the side of the catheter assembly or along a short central lumen or a removable lumen.

Moving from the distal end of the catheter assembly 100A of FIG. 4 to the proximal end, a priming apparatus 1400 can be disposed over an impeller assembly 116A. As explained above, the impeller assembly 116A can include an expandable cannula or housing and an impeller with one or more blades. As the impeller rotates, blood can be pumped proximally (or distally in some implementations) to function as a cardiac assist device.

FIG. 4 also shows one example of a priming apparatus 1400 disposed over the impeller assembly 116A near the distal end 170A of the elongate body 174A. FIG. 4A is an enlarged view of the priming apparatus 1400 shown in FIG. 4. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. However, in some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400.

A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter assembly 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter assembly 100A can be removed from the priming housing 1400 before a percutaneous heart procedure is performed, e.g., before the pump is activated to pump blood. The embodiments disclosed herein may be implemented such that the total time for infusing the system is minimized or reduced. For example, in some implementations, the time to fully infuse the system can be about six minutes or less. In other implementations, the time to infuse can be about three minutes or less. In yet other implementations, the total time to infuse the system can be about 45 seconds or less. It should be appreciated that lower times to infuse can be advantageous for use with cardiovascular patients.

With continued reference to FIG. 4, the elongate body 174A extends proximally from the impeller assembly 116A to an infusate device 195 configured to allow for infusate to enter the catheter assembly 100A and for waste fluid to leave the catheter assembly 100A. A catheter body 120A (which also passes through the elongate body 174A) can extend proximally and couple to a driven assembly 201. The driven assembly 201 can be configured to receive torque applied by a drive assembly 203, which is shown as being decoupled from the driven assembly 201 and the catheter assembly 100A in FIG. 4. Although not shown in FIG. 4, a drive shaft can extend from the driven assembly 201 through the catheter body 120A to couple to an impeller shaft at or proximal to the impeller assembly 116A. The catheter body 120A can pass within the elongate catheter body 174A such that the external catheter body 174A can axially translate relative to the catheter body 120A.

In addition, FIG. 4 illustrates a guidewire 235 extending from a proximal guidewire opening 237 in the driven assembly 201. Before inserting the catheter assembly 100A into a patient, a clinician may insert the guidewire 235 through the patient's vascular system to the heart to prepare a path for the operative device (e.g., the impeller assembly 116A) to the heart. In some embodiments, the catheter assembly can include a guidewire guide tube (see FIG. 12) passing through a central internal lumen of the catheter assembly 100A from the proximal guidewire opening 237. The guidewire guide tube can be pre-installed in the catheter assembly 100A to provide the clinician with a preformed pathway along which to insert the guidewire 235. Thus, in the embodiment of FIG. 4, the guidewire 235 can be advanced through a central lumen extending through the length of the catheter assembly 100A. Other embodiments may include different types of guide features, as explained herein.

In one approach, a guidewire is first placed in a conventional way, e.g., through a needle into a peripheral blood vessel, and along the path between that blood vessel and the heart and into a heart chamber, e.g., into the left ventricle. Thereafter, a distal end opening of the catheter assembly or guidewire guide can be advanced over the proximal end of the guidewire 235 to enable delivery to the catheter assembly 100A. After the proximal end of the guidewire 235 is urged proximally within the catheter assembly 100A and emerges from the guidewire opening 237 and/or guidewire guide, the catheter assembly 100A can be advanced into the patient. In one method, the guidewire guide is withdrawn proximally while holding the catheter assembly 100A. The guidewire guide is taken off of the catheter assembly 100A so that guidewire lumens from the proximal end to the distal end of the catheter assembly 100A are directly over the guidewire.

Alternatively, the clinician can thus insert the guidewire 235 through the proximal guidewire opening 237 and urge the guidewire 235 along the guidewire guide tube until the guidewire 235 extends from a distal guidewire opening (not shown) in the distal end of the catheter assembly 100A. The clinician can continue urging the guidewire 235 through the patient's vascular system until the distal end of the guidewire 235 is positioned in the desired chamber of the patient's heart. As shown in FIG. 4, a proximal end portion of the guidewire 235 can extend from the proximal guidewire opening 237. Once the distal end of the guidewire 235 is positioned in the heart, the clinician can maneuver the impeller assembly 116A over the guidewire 235 until the impeller assembly 116A reaches the distal end of the guidewire 235 in the heart. The clinician can remove the guidewire 235 and the guidewire guide tube. The guidewire guide tube can also be removed before or after the guidewire 235 is removed in some implementations. Still other arrangements for inserting the guidewire 235 through different types of guide features are explained in more detail below.

After removing at least the guidewire 235, the clinician can activate a motor to rotate the impeller and begin operation of the pump.

One problem that arises when using the guidewire 235 to guide the operative device to the heart is that a central lumen or tube (e.g., a guidewire guide) is typically formed to provide a path for the guidewire 235. In some implementations, it may be inconvenient or inoperable to provide a motor or drive assembly having a lumen through which the guidewire 235 can pass. Moreover, in some implementations, it may be desirable to provide the motor or drive assembly separate from the catheter assembly 100A, e.g., for manufacturing or economic purposes. Thus, it can be advantageous to provide a means to couple the drive assembly 203 to the driven assembly 201, while enabling the use of a guidewire guide through which a guidewire may be passed. Preferably, the drive assembly 203 can be securely coupled to the driven assembly 201 such that vibratory, axial, or other external forces do not decouple the drive assembly 203 from the driven assembly 201 during operation. Moreover, the coupling should preferably allow a motor to operate effectively so that the drive shaft is rotated at the desired speed and with the desired torque.

FIG. 5 illustrates one embodiment of a motor assembly 206 as the driven assembly 201 is being coupled to the drive assembly 203. The driven assembly 201 can include a flow diverter 205 and a flow diverter housing 207 that houses the flow diverter 205. The flow diverter 205 can be configured with a plurality of internal cavities, passages, and channels that are configured to route fluid to and from the patient during a medical procedure. As discussed below, an infusate can be directed into the flow diverter from a source of infusate. The infusate is a fluid that flows into the catheter body 120A to provide useful benefits, such as cooling moving parts and keeping blood from entering certain parts of the catheter assembly 100A. The infusate is diverted distally by flow channels in the flow diverter 205. Some of the infusate that flows distally is re-routed back through the catheter body 120A and may be diverted out of the catheter assembly 100A by the flow diverter 205. Moreover, a driven magnet 204 can be disposed within the flow diverter 205 in various embodiments. For example, the driven magnet 204 can be journaled for rotation in a proximal portion of the flow diverter housing 207. The proximal portion can project proximally of a proximal face of a distal portion of the flow diverter housing 207. In other embodiments, the driven magnet 204 can be disposed outside the flow diverter 205. The driven magnet 204 can be configured to rotate freely relative to the flow diverter 205 and/or the flow diverter housing 207. The catheter body 120A can extend from a distal end of the flow diverter housing 207. Further, a drive shaft 208 can pass through the catheter body 120A from the proximal end of the flow diverter housing 207 to the distal end 170A of the elongate body 174A. The drive shaft 208 can be configured to drive the impeller located at the distal end of the catheter assembly 100A. In some embodiments, a distal end of the drive shaft 208 can couple to an impeller shaft, which rotates the impeller.

The drive assembly 203 can include a drive housing or a motor housing 211 having an opening 202 in a cap 212 of the motor housing 211. The motor housing 211 can also have a sliding member 213, which can be configured to couple to the patient's body by way of, e.g., a connector 291 coupled to an adhesive or bandage on the patient's body. Because the motor and motor housing 211 can have a relatively high mass, it can be important to ensure that the motor housing 211 is stably supported. In one implementation, therefore, the motor housing 211 can be supported by the patient's body by way of the sliding member 213 and the connector 291 shown in FIG. 4. The sliding member 213 can slide along a track 214 located on a portion of the motor housing 211, such that relative motion between the motor assembly 206 and the patient does not decouple the sliding member 213 from the patient's body. The sliding member 213 and connector 291 can therefore be configured to provide a structural interface between the motor housing 206 and a platform for supporting the motor housing 211. As explained above, in some arrangements, the platform supporting the motor housing 211 can be the patient, since the motor housing 211 may be positioned quite close to the insertion point. In other arrangements, however, the platform supporting the motor housing 211 may be an external structure.

To couple the drive assembly 203 to the driven assembly 201, the clinician or user can insert the proximal portion of the flow diverter 205 into the opening 202 in the cap 212 of the motor housing 212. After passing through the opening 202, the proximal portion of the flow diverter can reside within a recess formed within the motor housing 211. In some implementations, a securement device is configured to lock or secure the drive assembly 203 to the driven assembly 201 once the driven assembly 201 is fully inserted into the drive assembly 203. In other implementations, the securement device can be configured to secure the drive assembly 203 to the driven assembly 201 by inserting the driven assembly 201 into the drive assembly 203 and then rotating the drive assembly 203 with respect to the driven assembly. In some implementations, coupling the drive assembly 203 to the driven assembly 201 may be irreversible, such that there may be no release mechanism to decouple the drive assembly 203 from the driven assembly 201. In implementations without a release mechanism, the catheter assembly 100A (including the driven assembly 201) and the motor housing 211 may be disposable components. In other implementations, however, a release mechanism may be provided to remove the drive assembly 203 from the driven assembly 201. The drive assembly 203 can thereby be used multiple times in some embodiments.

Figure 6:
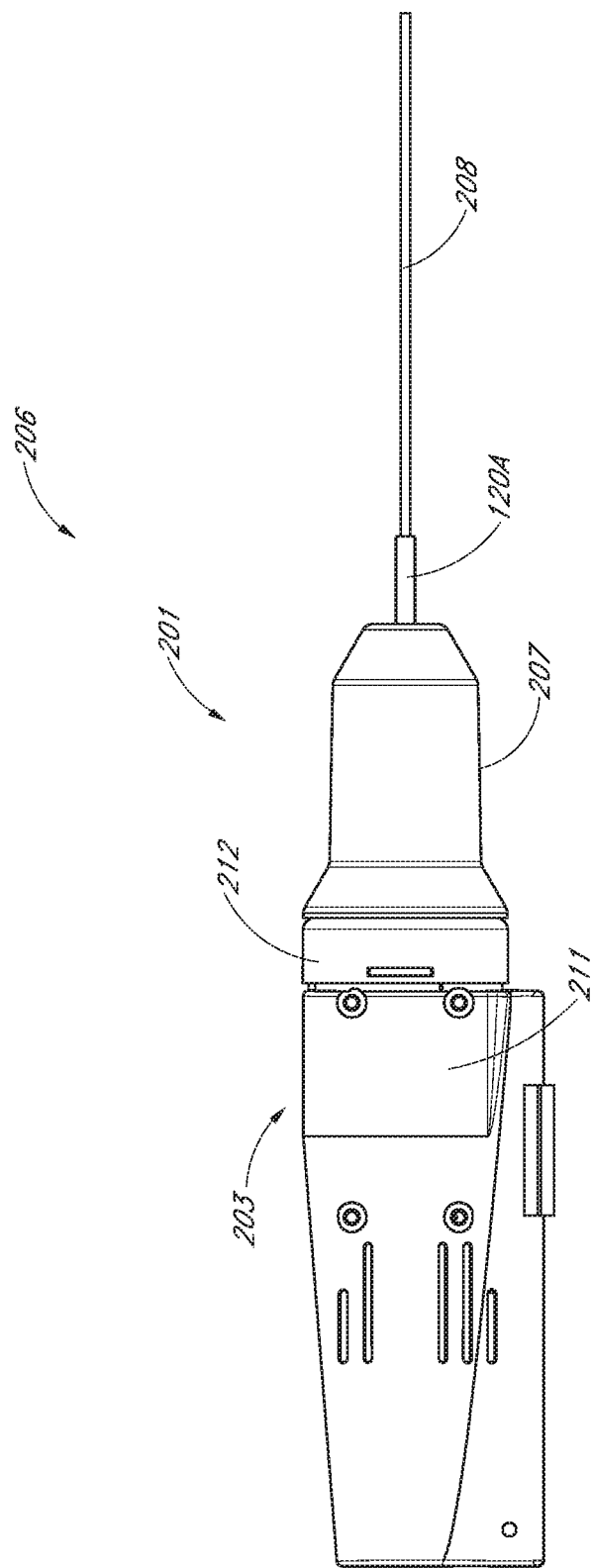
FIG. 6 is a 3D perspective view of the motor assembly once the drive assembly has been coupled and secured to the driven assembly.

FIG. 6 illustrates the motor assembly 206 in the assembled state, e.g., after the drive assembly 203 has been secured to the driven assembly 201. When the drive assembly 203 is activated (e.g., a motor is activated to rotate an output shaft), the driven assembly 201, which is operably coupled to the drive assembly, is also activated. The activated driven assembly can cause the drive shaft 208 to rotate, which in turn causes the impeller to rotate to thereby pump blood through the patient.

Figure 7:
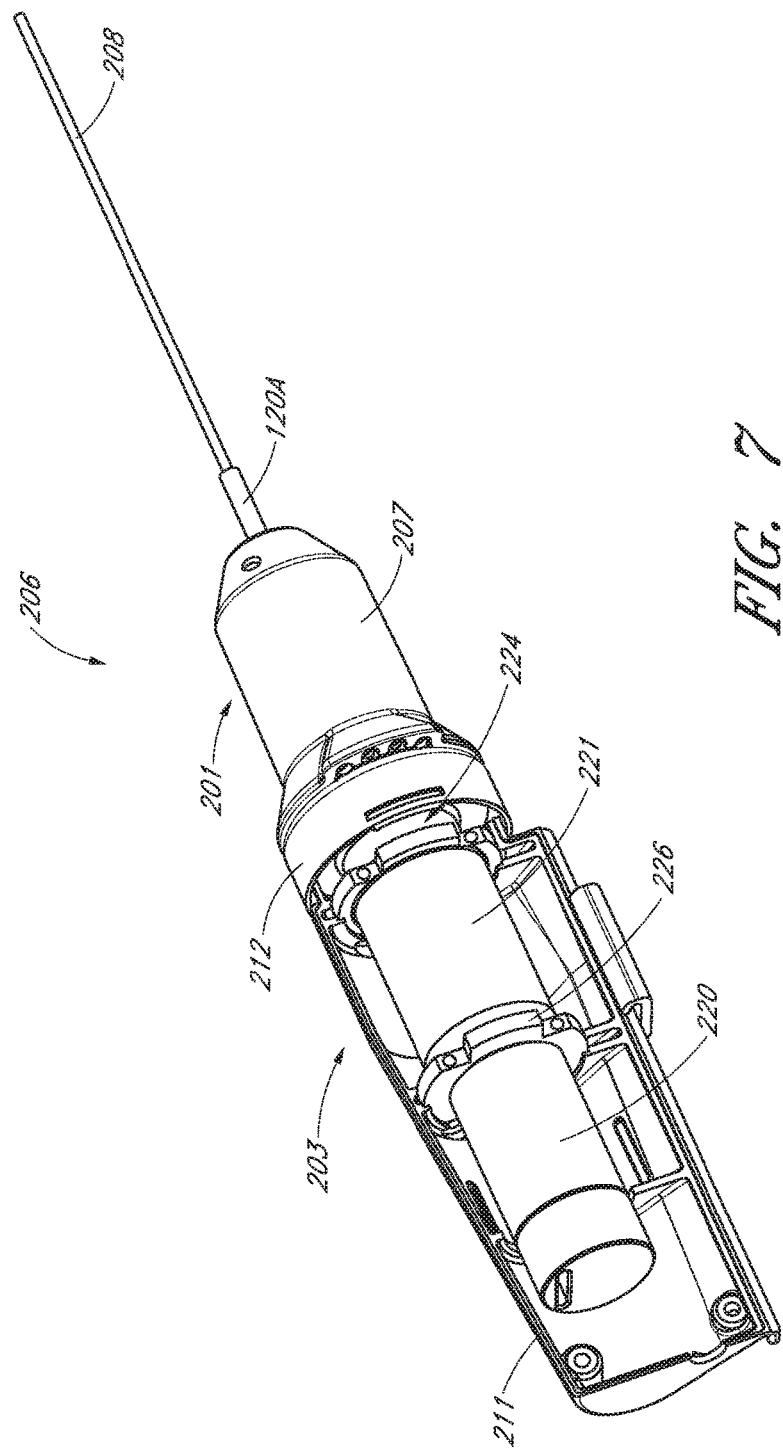
FIG. 7 is a 3D perspective view of the motor assembly of FIG. 6, wherein various components have been removed for ease of illustration.
Figure 8:
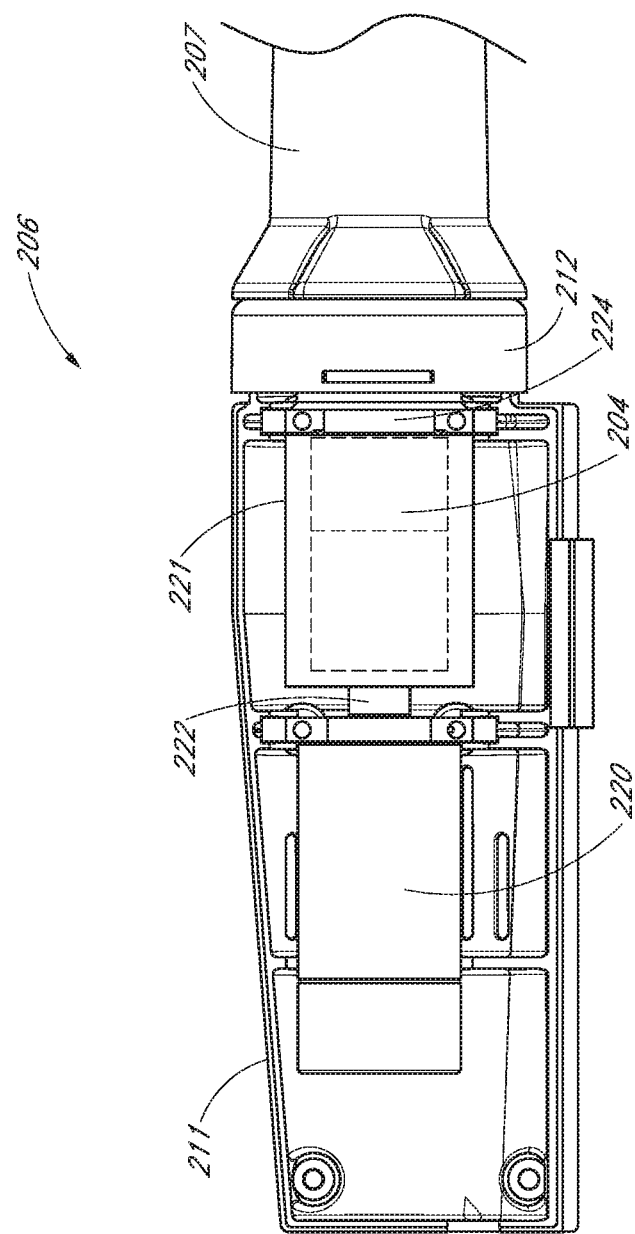
FIG. 8 is a plan view of the motor assembly that illustrates a motor, a drive magnet and a driven magnet.

FIGS. 7-8 illustrate the motor assembly 206 with one wall of the motor housing 211 removed so that various internal components in the housing 211 can be better illustrated. A motor 220 can be positioned within the housing 211 and mounted by way of a motor mount 226. The motor 220 can operably couple to a drive magnet 221. For example, the motor 220 can include an output shaft 222 that rotates the drive magnet 221. In some implementations, the drive magnet 221 can rotate relative to the motor mount 226 and the motor housing 211. Further, in some arrangements, the drive magnet 221 can be free to translate axially between the motor mount and a barrier 224. One advantage of the translating capability is to enable the drive magnet 221 and the driven magnet 204 to self-align by way of axial translation. The barrier 224 can be mounted to the motor housing 211 and at least partially within the cap 212 to support at least the drive magnet 221. In other implementations, the drive assembly 203 can comprise a plurality of motor windings configured to induce rotation of the drive magnet 221. In still other embodiments, motor windings can operate directly on a driven magnet within the driven assembly 201. For example, the windings can be activated in phases to create an electric field and thereby commutate the driven magnet.

In FIG. 8, the drive magnet 221 is illustrated in phantom, such that the driven magnet 204 can be seen disposed within the drive magnet 221. Although not illustrated, the poles of the drive magnet 221 can be formed on an interior surface of the drive magnet 221, and the poles of the driven magnet 204 can be formed on an exterior surface of the driven magnet 204. As the drive magnet 221 rotates, the poles of the drive magnet 221 can magnetically engage with corresponding, opposite poles of the driven magnet 204 to cause the driven magnet 204 to rotate with, or follow, the drive magnet 221. Because the driven magnet 204 can be mechanically coupled to the drive shaft 208, rotation of the drive magnet 221 can cause the driven magnet 204 and the drive shaft 208 to rotate at a speed determined in part by the speed of the motor 220. Furthermore, when the driven magnet 204 is inserted into the drive magnet 221, the poles of each magnet can cause the drive magnet 221 and the driven magnet 204 to self-align. The magnetic forces between the drive magnet 221 and the driven magnet 204 can assist in coupling the drive assembly 203 to the driven assembly 201.

Figure 9:
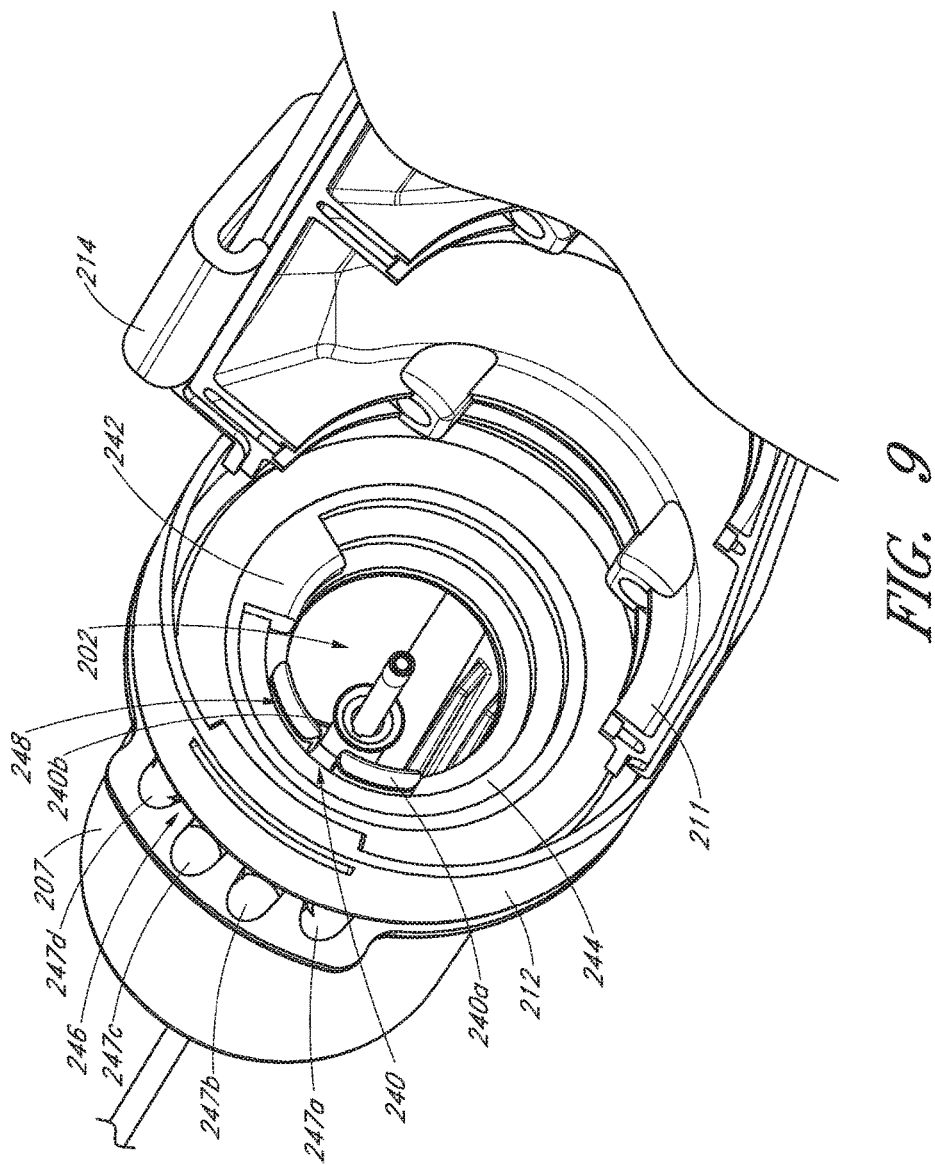
FIG. 9 is a 3D perspective view of a first securement device configured to secure the drive assembly to the driven assembly.

Turning to FIG. 9, a 3D perspective view of various components at the interface between the drive assembly 203 and the driven assembly 201 is shown. Various components have been hidden to facilitate illustration of one means to secure the drive assembly 203 to the driven assembly 201. A first securement device 240 is illustrated in FIG. 9. The first securement device can comprise a first projection 240a and a second projection 240b. Furthermore, a locking recess 244 can be formed in the cap 212 around at least a portion of a perimeter of the opening 202. A lip 242 can also extend from the perimeter at least partially into the opening 202. As shown, the lip 242 can also extend proximally from the locking recess 244 such that a step is formed between the locking recess 244 and the lip 242. Further, a flange 246 can be coupled to or formed integrally with the flow diverter housing 207. The flange 246 can include a plurality of apertures 247a, 247b, 247c, 247d that are configured to permit tubes and cables to pass therethrough to fluidly communicate with lumens within the flow diverter 205. In some implementations, three tubes and one electrical cable can pass through the apertures 247a-d. For example, the electrical cable can be configured to electrically couple to a sensor within the catheter assembly 100A, e.g., a pressure sensor. The three tubes can be configured to carry fluid to and from the catheter assembly 100A. For example, a first tube can be configured to carry infusate into the catheter assembly 100A, a second tube can be configured to transport fluids to the pressure sensor region, and the third tube can be configured to transport waste fluid out of the catheter assembly 100A. Although not illustrated, the tubes and cable(s) can pass through the apertures 247a-d of the flange 246 and can rest against the motor housing 211. By organizing the routing of the tubes and cable(s), the apertures 247a-d can advantageously prevent the tubes and cable(s) from becoming entangled with one another or with other components of the catheter pump system.

When the driven assembly 201 is inserted into the opening 202, the first and second projections 240a, 240b can pass through the opening and engage the locking recess 244. In some implementations, the projections 240a, 240b and the locking recess 244 can be sized and shaped such that axial translation of the projections 240a, 240b through the opening 202 causes a flange or tab 248 at a distal end of each projection 240a, 240b to extend over the locking recess 244. Thus, in some embodiments, once the projections 240a, 240b are inserted through the opening 202, the tabs 248 at the distal end of the projections 240a, 240b are biased to deform radially outward to engage the locking recess 244 to secure the driven assembly 201 to the drive assembly 203.

Once the driven assembly 201 is secured to the drive assembly 203, the flow diverter housing 207 can be rotated relative to the motor cap 212. By permitting relative rotation between the driven assembly 201 and the drive assembly 203, the clinician is able to position the impeller assembly 116A within the patient at a desired angle or configuration to achieve the best pumping performance. As shown in FIG. 9, however, the lip 242 can act to restrict the relative rotation between the driven assembly 201 (e.g., the flow diverter housing 207) and the drive assembly 203 (e.g. the cap 212 and the motor housing 211). As illustrated, the flange 246 and apertures 247a-d can be circumferentially aligned with the projections 240a, 240b. Further, the lip 242 can be circumferentially aligned with the sliding member 213, the track 214, and the connector 291 of the motor housing 211. If the flange 246 and projections 240a, 240b are rotated such that they circumferentially align with the lip 242, then the tubes and cable(s) that extend from the apertures 247a-d may become entangled with or otherwise obstructed by the sliding member 213 and the connector 291. Thus, it can be advantageous to ensure that the sliding member 213 and the connector 291 (or any other components on the outer surface of the housing 211) do not interfere or obstruct the tubes and cable(s) extending out of the apertures 247a-d of the flange 246. The lip 242 formed in the cap 212 can act to solve this problem by ensuring that the flange 246 is circumferentially offset from the sliding member 213 and the connector 291. For example, the flow diverter housing 207 can be rotated until one of the projections 240a, 240b bears against a side of the lip 242. By preventing further rotation beyond the side of the lip 242, the lip 242 can ensure that the flange 246 and apertures 247a-d are circumferentially offset from the sliding member 213, the track 214, and the connector 291.

In one embodiment, once the catheter assembly 100A is secured to the motor housing 211, the connection between the driven assembly 201 and the drive assembly 203 may be configured such that the drive assembly 203 may not be removed from the driven assembly 201. The secure connection between the two assemblies can advantageously ensure that the motor housing 211 is not accidentally disengaged from the catheter assembly 100A during a medical procedure. In such embodiments, both the catheter assembly 100A and the drive assembly 203 may preferably be disposable.

In other embodiments, however, it may be desirable to utilize a re-usable drive assembly 203. In such embodiments, therefore, the drive assembly 203 may be removably engaged with the catheter assembly 100A (e.g., engaged with the driven assembly 201). For example, the lip 242 may be sized and shaped such that when the drive assembly 203 is rotated relative to the driven assembly 201, the tabs 248 are deflected radially inward over the lip 242 such that the driven assembly 201 can be withdrawn from the opening 202. For example, the lip 242 may include a ramped portion along the sides of the lip 242 to urge the projections 240a, 240b radially inward. It should be appreciated that other release mechanisms are possible.

Figure 10A:
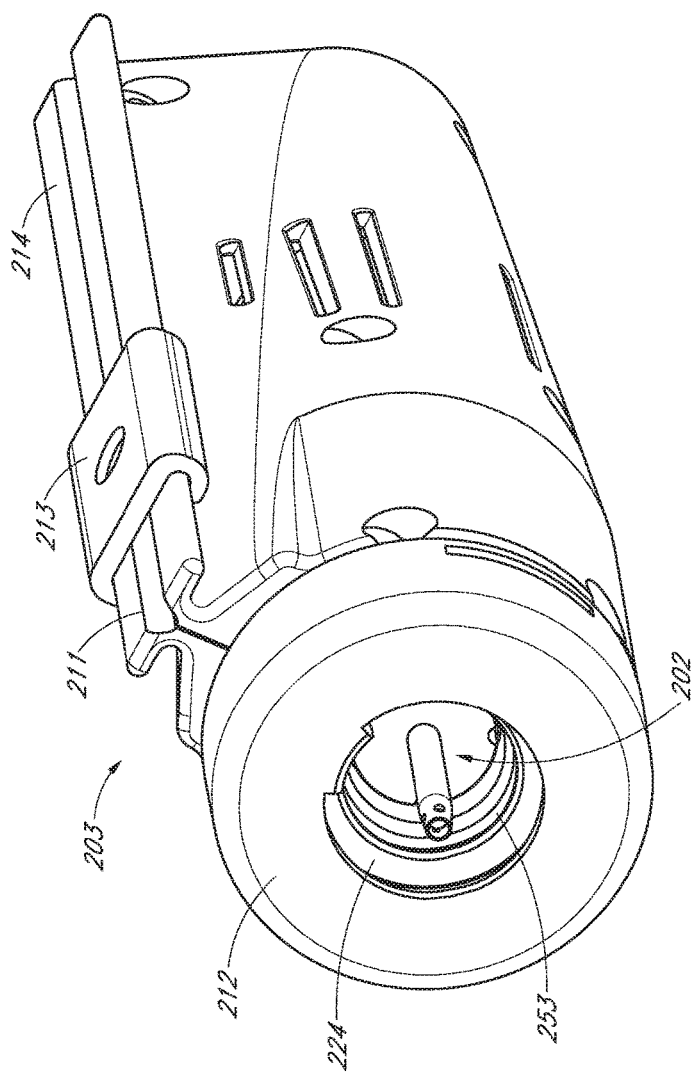
FIGS. 10A-10C are 3D perspective views of a second securement device configured to secure the drive assembly to the driven assembly.
Figure 10B:
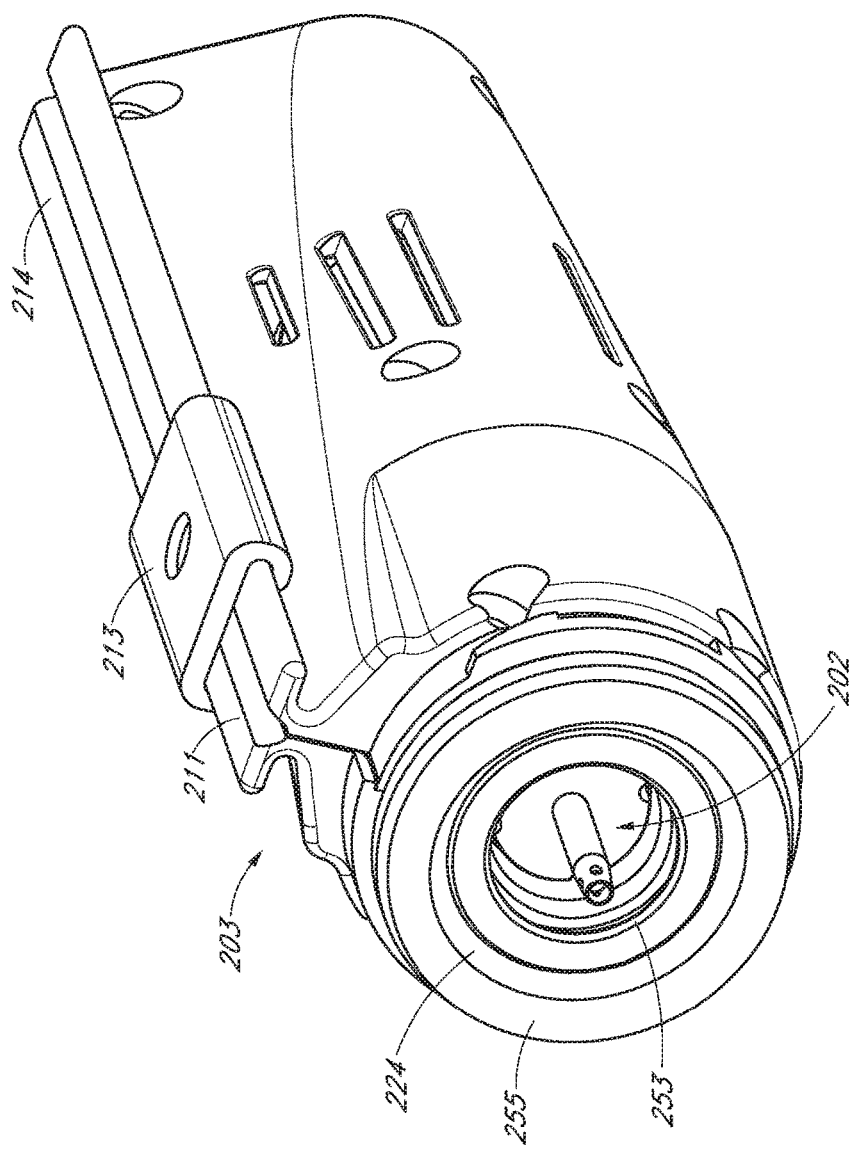
Figure 10C:
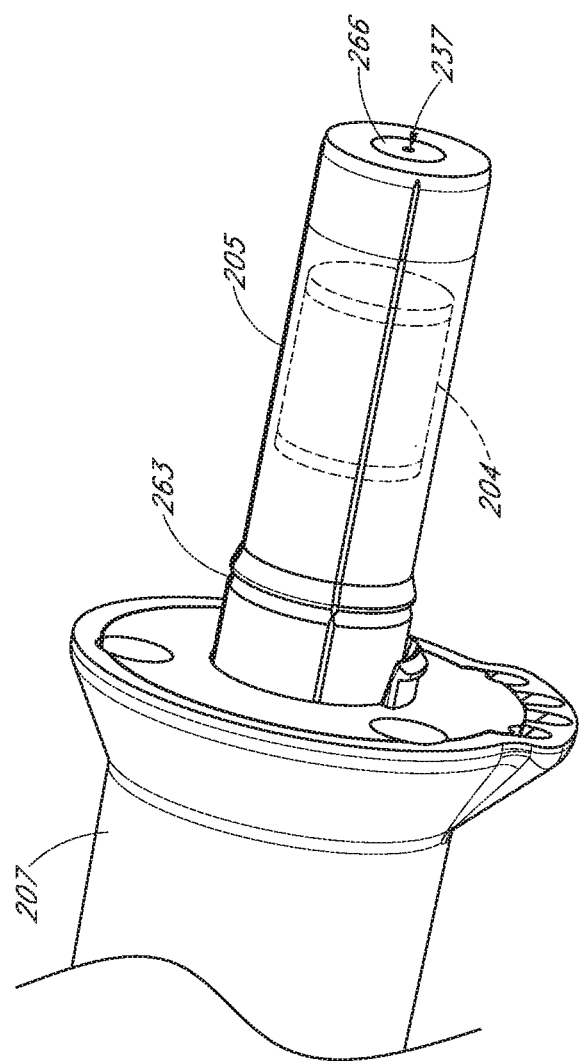

Turning to FIGS. 10A-10C, an additional means to secure the drive assembly 203 to the driven assembly 201 is disclosed. As shown in the 3D perspective view of FIG. 10A, a locking O-ring 253 can be mounted to the barrier 224 that is disposed within the motor housing 211 and at least partially within the cap 212. In particular, the locking O-ring 253 can be mounted on an inner surface of the drive or motor housing 203 surrounding the recess or opening 202 into which the driven assembly 212 can be received. As explained below, the locking O-ring can act as a detent mechanism and can be configured to be secured within an arcuate channel formed in an outer surface of the driven assembly 201, e.g., in an outer surface of the flow diverter 205 in some embodiments. In other embodiments, various other mechanisms can act as a detent to secure the driven assembly 201 to the drive assembly 203. For example, in one embodiment, a spring plunger or other type of spring-loaded feature may be cut or molded into the barrier 224, in a manner similar to the locking O-ring 253 of FIGS. 10A-10C. The spring plunger or spring-loaded feature can be configured to engage the arcuate channel, as explained below with respect to FIG. 10C. Skilled artisans will understand that other types of detent mechanisms can be employed.

FIG. 10B illustrates the same 3D perspective of the drive assembly 203 as shown in FIG. 10A, except the cap 212 has been hidden to better illustrate the locking O-ring 253 and a second, stabilizing O-ring 255. The O-ring 255 is an example of a damper that can be provided between the motor 220 and the catheter assembly 100A. The damper can provide a vibration absorbing benefit in some embodiments. In other embodiment, the damper may reduce noise when the pump is operating. The damper can also both absorb vibration and reduce noise in some embodiments. The stabilizing O-ring 255 can be disposed within the cap 212 and can be sized and shaped to fit along the inner recess forming the inner perimeter of the cap 212. The stabilizing O-ring 255 can be configured to stabilize the cap 212 and the motor housing 211 against vibrations induced by operation of the motor 220. For example, as the motor housing 211 and/or cap 212 vibrate, the stabilizing O-ring 255 can absorb the vibrations transmitted through the cap 212. The stabilizing O-ring 255 can support the cap 212 to prevent the cap from deforming or deflecting in response to vibrations. In some implementations, the O-ring 255 can act to dampen the vibrations, which can be significant given the high rotational speeds involved in the exemplary device.

In further embodiments, a damping material can also be applied around the motor 220 to further dampen vibrations. The damping material can be any suitable damping material, e.g., a visco-elastic or elastic polymer. For example, the damping material may be applied between the motor mount 226 and the motor 220 in some embodiments. In addition, the damping material may also be applied around the body of the motor 220 between the motor 220 and the motor housing 211. In some implementations, the damping material may be captured by a rib formed in the motor housing 211. The rib may be formed around the motor 220 in some embodiments.

Turning to FIG. 10C, a proximal end of the driven assembly 201 is shown. As explained above, the flow diverter 205 (or the flow diverter housing in some embodiments) can include an arcuate channel 263 formed in an outer surface of the flow diverter 205. The arcuate channel 263 can be sized and shaped to receive the locking O-ring 253 when the flow diverter 205 is inserted into the opening 202 of the drive assembly 203. As the flow diverter 205 is axially translated through the recess or opening 202, the locking O-ring 253 can be urged or slid over an edge of the channel 263 and can be retained in the arcuate channel 263. Thus, the locking O-ring 253 and the arcuate channel 263 can operate to act as a second securement device. Axial forces applied to the motor assembly 206 can thereby be mechanically resisted, as the walls of the arcuate channel 263 bear against the locking O-ring 253 to prevent the locking o-ring 253 from translating relative to the arcuate channel 263. In various arrangements, other internal locking mechanisms (e.g., within the driven assembly 201 and/or the drive assembly 203) can be provided to secure the driven and drive assemblies 201, 203 together. For example, the driven magnet 204 and the drive magnet 221 may be configured to assist in securing the two assemblies together, in addition to aligning the poles of the magnets. Other internal locking mechanisms may be suitable.

FIG. 10C also illustrates a resealable member 266 disposed within the proximal end portion of the driven assembly 201, e.g., the proximal end of the catheter assembly 100A as shown in FIG. 4. As in FIG. 4, the proximal guidewire opening 237 can be formed in the resealable member 266. As explained above with respect to FIG. 4, the guidewire 235 can be inserted through the proximal guidewire opening 237 and can be maneuvered through the patient's vasculature. After guiding the operative device of the pump to the heart, the guidewire 235 can be removed from the catheter assembly 100A by pulling the guidewire 235 out through the proximal guidewire opening 237. Because fluid may be introduced into the flow diverter 205, it can be advantageous to seal the proximal end of the flow diverter 205 to prevent fluid from leaking out of the catheter assembly 100A. The resealable member 266 can therefore be formed of an elastic, self-sealing material that is capable of closing and sealing the proximal guidewire opening 237 when the guidewire 235 is removed. The resealable member can be formed of any suitable material, such as an elastomeric material. In some implementations, the resealable member 266 can be formed of any suitable polymer, e.g., a silicone or polyisoprene polymer. Skilled artisans will understand that other suitable materials may be used.

FIG. 11 illustrates yet another embodiment of a motor assembly 206A coupled to a catheter assembly. In FIG. 11, a flow diverter is disposed over and coupled to a catheter body 271 that can include a multi-lumen sheath configured to transport fluids into and away from the catheter assembly. The flow diverter 205A can provide support to the catheter body 271 and a drive shaft configured to drive the impeller assembly. Further, the motor assembly 206A can include a motor 220A that has a hollow lumen therethrough. Unlike the embodiments disclosed in FIGS. 4-10C, the guidewire 235 may extend through the proximal guidewire opening 237A formed proximal to the motor 220A, rather than between the motor 220A and the flow diverter 205A. A rescalable member 266A may be formed in the proximal guidewire opening 237A such that the rescalable member 266A can close the opening 237A when the guidewire 235 is removed from the catheter assembly. A rotary seal 273 may be disposed inside a lip of the flow diverter 205A. The rotary seal 273 may be disposed over and may contact a motor shaft extending from the motor 220A. The rotary seal 273 can act to seal fluid within the flow diverter 205A. In some embodiments, a hydrodynamic seal can be created to prevent fluid from breaching the rotary seal 273.

In the implementation of FIG. 11, the motor 220A can be permanently secured to the flow diverter 205A and catheter assembly. Because the proximal guidewire opening 237 is positioned proximal the motor, the motor 220A need not be coupled with the catheter assembly in a separate coupling step. The motor 220A and the catheter assembly can thus be disposable in this embodiment. The motor 220A can include an output shaft and rotor magnetically coupled with a rotatable magnet in the flow diverter 205A. The motor 220A can also include a plurality of windings that are energized to directly drive the rotatable magnet in the flow diverter 205A.

Figure 12B:
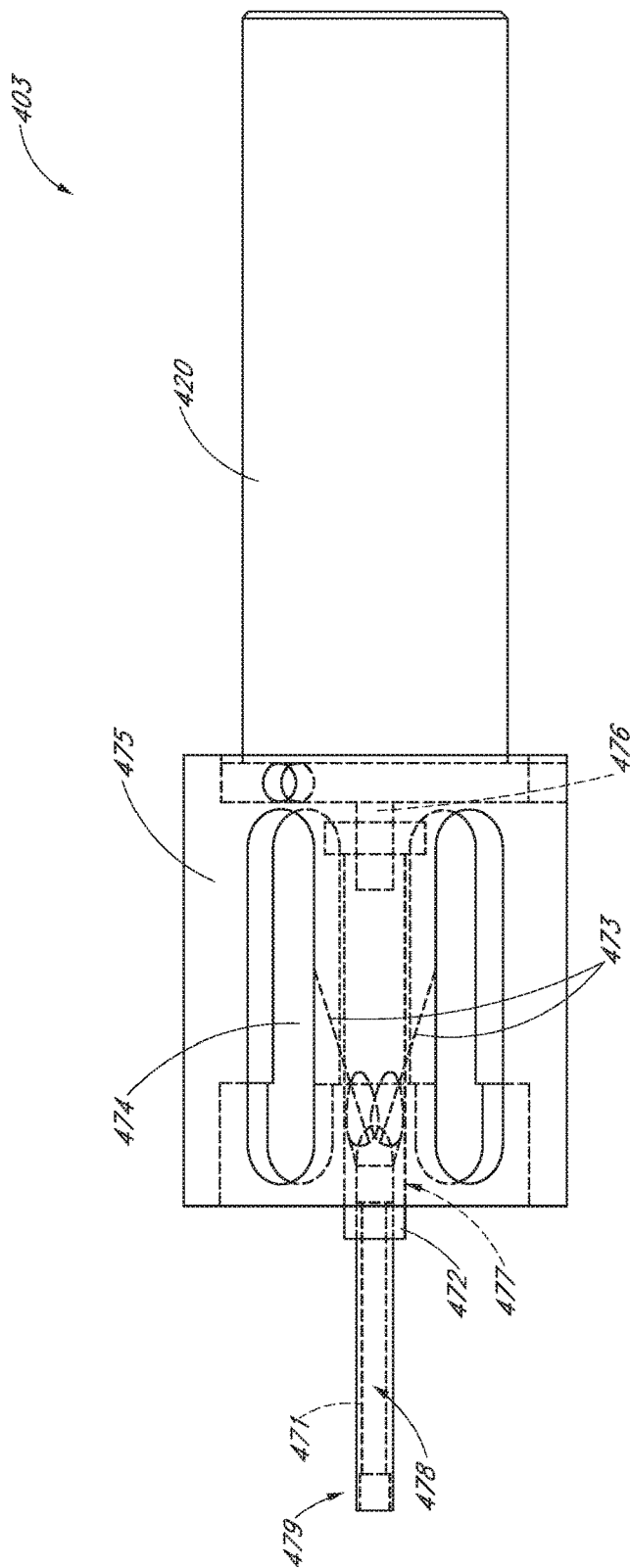

FIGS. 12A-12B illustrate another embodiment of a motor coupling having a driven assembly 401 and a drive assembly 403. Unlike the implementations disclosed in FIGS. 4-10C, however, the embodiment of FIGS. 12A-12B can include a mechanical coupling disposed between an output shaft of a motor and a proximal end of a flexible drive shaft or cable. Unlike the implementations disclosed in FIG. 11, however, the embodiment of FIGS. 12A-12B can include a guidewire guide tube that terminates at a location distal to a motor shaft 476 that extends from a motor 420. As best shown in FIG. 12B, an adapter shaft 472 can operably couple to the motor shaft 476 extending from the motor 420. A distal end portion 477 of the adapter shaft 472 can mechanically couple to a proximal portion of an extension shaft 471 having a central lumen 478 therethrough. As shown in FIG. 12B, one or more trajectories 473 can be formed in channels within a motor housing 475 at an angle to the central lumen 478 of the extension shaft 471. The motor housing 475 can enclose at least the adapter shaft 472 and can include one or more slots 474 formed through a wall of the housing 475.

In some implementations, a guidewire (not shown in FIG. 12B) may pass through the guidewire guide tube from the distal end portion of the catheter assembly and may exit the assembly through the central lumen 478 near the distal end portion 477 of the adapter shaft 472 (or, alternatively, near the proximal end portion of the extension shaft 471). In some embodiments, one of the extension shaft 471 and the adapter shaft 472 may include a resealable member disposed therein to reseal the lumen through which the guidewire passes, as explained above. In some embodiments, the extension shaft 471 and the adapter shaft 472 can be combined into a single structure. When the guidewire exits the central lumen 478, the guidewire can pass along the angled trajectories 473 which can be formed in channels and can further pass through the slots 474 to the outside environs. The trajectories 473 can follow from angled ports in the adapter shaft 472. A clinician can thereby pull the guidewire through the slots 474 such that the end of the guidewire can easily be pulled from the patient after guiding the catheter assembly to the heart chamber or other desired location. Because the guidewire may extend out the side of the housing 475 through the slots, the motor shaft 476 and motor 420 need not include a central lumen for housing the guidewire. Rather, the motor shaft 476 may be solid and the guidewire can simply pass through the slots 474 formed in the side of the housing 475.

Furthermore, the drive assembly 403 can mechanically couple to the driven assembly 401. For example, a distal end portion 479 of the extension shaft 471 may be inserted into an opening in a flow diverter housing 455. The distal end portion 479 of the extension shaft 471 may be positioned within a recess 451 and may couple to a proximal end of a drive cable 450 that is mechanically coupled to the impeller assembly. A rotary seal 461 may be positioned around the opening and can be configured to seal the motor 420 and/or motor housing 475 from fluid within the flow diverter 405. Advantageously, the embodiments of FIGS. 12A-B allow the motor 420 to be positioned proximal of the rotary seal in order to minimize or prevent exposing the motor 420 to fluid that may inadvertently leak from the flow diverter. It should be appreciated that the extension shaft 471 may be lengthened in order to further isolate or separate the motor 420 from the fluid diverter 405 in order to minimize the risk of leaking fluids.

Figure 13:
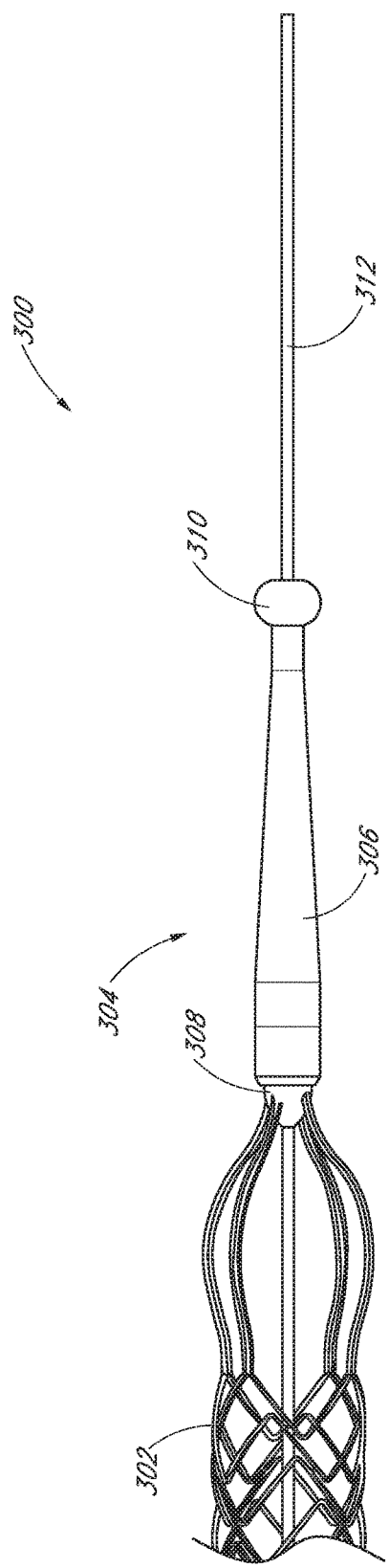
FIG. 13 is a side view of a distal tip member disposed at a distal end of the catheter assembly, according to one embodiment.

Turning to FIG. 13, further features that may be included in various embodiments are disclosed. FIG. 13 illustrates a distal end portion 300 of a catheter assembly, such as the catheter assembly 100A described above. As shown a cannula housing 302 can couple to a distal tip member 304. The distal tip member 304 can be configured to assist in guiding the operative device of the catheter assembly, e.g., an impeller assembly (which can be similar to or the same as impeller assembly 116A), along the guidewire 235. The exemplary distal tip member 304 is formed of a flexible material and has a rounded end to prevent injury to the surrounding tissue. If the distal tip member 304 contacts a portion of the patient's anatomy (such as a heart wall or an arterial wall), the distal tip member 304 will safely deform or bend without harming the patient. The tip can also serve to space the operative device away from the tissue wall. In addition, a guide feature or guidewire guide tube 312 can be provided. The guidewire guide tube 312, discussed above with reference to FIG. 4, can extend through a central lumen of the catheter assembly. Thus, the guidewire guide tube 312 can pass through the impeller shaft (not shown, as the impeller is located proximal to the distal end portion 300 shown in FIG. 13) and a lumen formed within the distal tip member 304. Indeed, the guidewire guide tube 312 of FIG. 13 can comprise a central lumen extending throughout the length of the catheter assembly 100A. In the embodiment of FIG. 13, the guidewire guide tube 312 may extend distally past the distal end of the distal tip member 304. As explained above, in various embodiments, the clinician can introduce a proximal end of the guidewire into the distal end of the guidewire guide tube 312, which in FIG. 13 extends distally beyond the tip member 304. Once the guidewire 235 has been inserted into the patient, the guidewire guide tube 312 can be removed from the catheter assembly in some implementations.

The distal tip member 304 can comprise a flexible, central body 306, a proximal coupling member 308, and a rounded tip 310 at the distal end of the tip member 304. The central body 306 can provide structural support for the distal tip member 304. The proximal coupling member 308 can be coupled to or integrally formed with the central body 306. The proximal coupling member 308 can be configured to couple the distal end of the cannula housing 302 to the distal tip member 304. The rounded tip 310, also referred to as a ball tip, can be integrally formed with the central body 306 at a distal end of the tip member 304. Because the rounded tip 310 is flexible and has a round shape, if the tip member 304 contacts or interacts with the patient's anatomy, the rounded tip 310 can have sufficient compliance so as to deflect away from the anatomy instead of puncturing or otherwise injuring the anatomy. As compared with other potential implementations, the distal tip member 304 can advantageously include sufficient structure by way of the central body 306 such that the tip member 304 can accurately track the guidewire 235 to position the impeller assembly within the heart. Yet, because the tip member 304 is made of a flexible material and includes the rounded tip 310, any mechanical interactions with the anatomy can be clinically safe for the patient.

One potential problem with the embodiment of FIG. 13 is that it can be difficult for the clinician to insert the guidewire into the narrow lumen of the guidewire guide tube 312. Since the guidewire guide tube 312 has a small inner diameter relative to the size of the clinician's hands, the clinician may have trouble inserting the guidewire into the distal end of the guidewire guide tube 312, which extends past the distal end of the tip member 304 in FIG. 13. In addition, when the clinician inserts the guidewire into the guidewire guide tube 312, the distal edges of the guidewire guide tube 312 may scratch or partially remove a protective coating applied on the exterior surface of the guidewire. Damage to the coating on the guidewire may harm the patient as the partially uncoated guidewire is passed through the patient's vasculature. Accordingly, it can be desirable in various arrangements to make it easier for the clinician to insert the guidewire into the distal end of the catheter assembly, and/or to permit insertion of the guidewire into the catheter assembly while maintaining the protective coating on the guidewire.

Additionally, as explained herein, the cannula housing 302 (which may form part of an operative device) may be collapsed into a stored configuration in some embodiments such that the cannula housing is disposed within an outer sheath. When the cannula housing 302 is disposed within the outer sheath, a distal end or edge of the outer sheath may abut the tip member 304. In some cases, the distal edge of the outer sheath may extend over the tip member 304A, or the sheath may have an outer diameter such that the distal edge of the outer sheath is exposed. When the sheath is advanced through the patient's vasculature, the distal edge of the outer sheath may scratch, scrape, or otherwise harm the anatomy. There is a therefore a need to prevent harm to the patient's anatomy due to scraping of the distal edge of the sheath against the vasculature.

Figure 14:
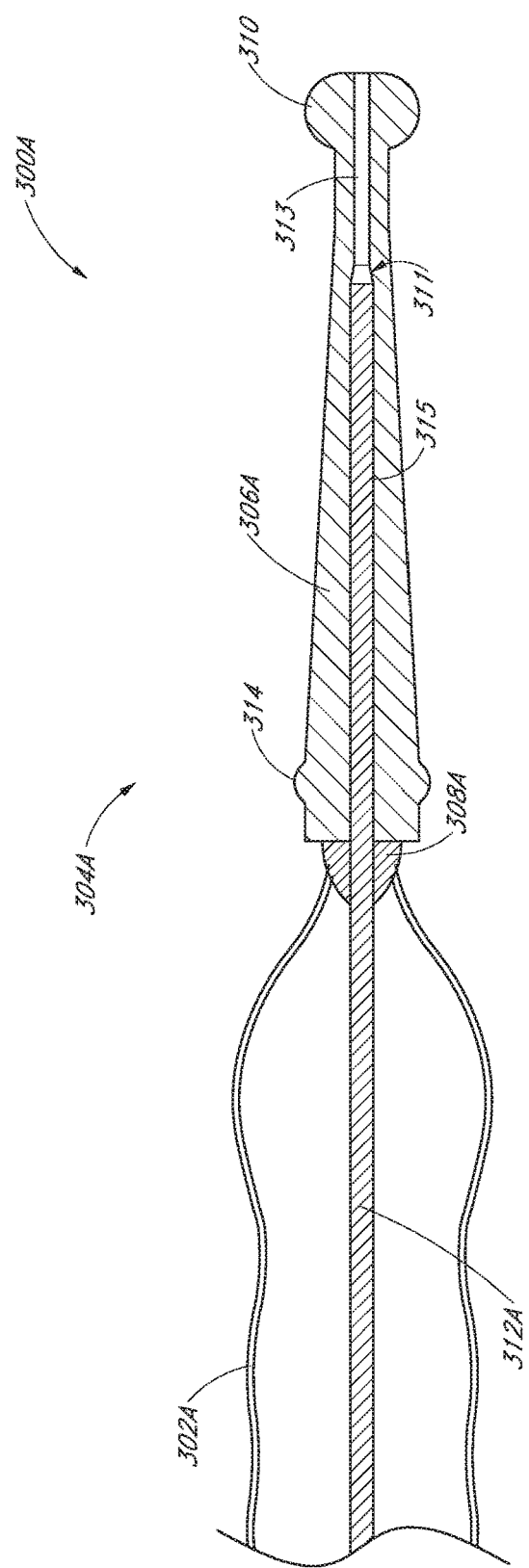
FIG. 14 is a side cross-sectional view of a distal tip member disposed at a distal end of the catheter assembly, according to another embodiment.

FIG. 14 is a side cross-sectional view of a distal tip member 304A disposed at a distal end 300A of the catheter assembly, according to another embodiment. Unless otherwise noted, the reference numerals in FIG. 14 may refer to components similar to or the same as those in FIG. 13. For example, as with FIG. 13, the distal tip member 304A can couple to a cannula housing 302A. The distal tip member 304A can include a flexible, central body 306A, a proximal coupling member 308A, and a rounded tip 310A at the distal end of the tip member 304A. Furthermore, as with FIG. 13, a guide feature or guidewire guide tube 312A can pass through the cannula housing 302A and a lumen passing through the distal tip member 304A.

However, unlike the embodiment of FIG. 13, the central body 306A can include a bump 314 disposed near a proximal portion of the tip member 304A. The bump 314 illustrated in FIG. 14 may advantageously prevent the outer sheath from scraping or scratching the anatomy when the sheath is advanced through the patient's vascular system. For example, when the cannula housing 302A is disposed within the outer sheath, the sheath will advance over the cannula housing 302A such that the distal edge or end of the sheath will abut or be adjacent the bump 314 of the tip member 304A. The bump 314 can act to shield the patient's anatomy from sharp edges of the outer sheath as the distal end 300A is advanced through the patient. Further, the patient may not be harmed when the bump 314 interact with the anatomy, because the bump 314 includes a rounded, smooth profile. Accordingly, the bump 314 in FIG. 14 may advantageously improve patient outcomes by further protecting the patient's anatomy.

Furthermore, the guidewire guide tube 312A of FIG. 14 does not extend distally past the end of the tip member 306A. Rather, in FIG. 14, the central lumen passing through the tip member 304A may include a proximal lumen 315 and a distal lumen 313. As shown in FIG. 14, the proximal lumen 315 may have an inner diameter larger than an inner diameter of the distal lumen 313. A stepped portion or shoulder 311 may define the transition between the proximal lumen 315 and the distal lumen 313. As illustrated in FIG. 14, the inner diameter of the proximal lumen 315 is sized to accommodate the guidewire guide tube 312A as it passes through a portion of the tip member 304A. However, the inner diameter of the distal lumen 313 in FIG. 14 is sized to be smaller than the outer diameter of the guidewire guide tube 312A such that the guidewire guide tube 312A is too large to pass through the distal lumen 313 of the tip member 304A. In addition, in some embodiments, the thickness of the guidewire guide tube 312A may be made smaller than the height of the stepped portion or shoulder 311, e.g., smaller than the difference between the inner diameter of the proximal lumen 315 and the inner diameter of the distal lumen 313. By housing the guidewire guide tube 312A against the shoulder 311, the shoulder 311 can protect the outer coating of the guidewire when the guidewire is inserted proximally from the distal lumen 313 to the proximal lumen 315.

The embodiment illustrated in FIG. 14 may assist the clinician in inserting the guidewire (e.g., the guidewire 235 described above) into the distal end 300A of the catheter assembly. For example, in FIG. 14, the guidewire guide tube 312A may be inserted through the central lumen of the catheter assembly. For example, the guidewire guide tube 312A may pass distally through a portion of the motor, the catheter body, the impeller assembly and cannula housing 302A, and through the proximal lumen 315 of the tip member 304A. The guidewire guide tube 312A may be urged further distally until the distal end of the guidewire guide tube 312A reaches the shoulder 311. When the distal end of the guidewire guide tube 312A reaches the shoulder 311, the shoulder 311 may prevent further insertion of the guidewire guide tube 312 in the distal direction. Because the inner diameter of the distal lumen 313 is smaller than the outer diameter of the guidewire guide tube 312A, the distal end of the guidewire guide tube 312A may be disposed just proximal of the shoulder 311, as shown in FIG. 14.

The clinician may insert the proximal end of the guidewire (such as the guidewire 235 described above) proximally through the distal lumen 313 passing through the rounded tip 310A at the distal end of the tip member 304A. Because the tip member 304A is flexible, the clinician can easily bend or otherwise manipulate the distal end of the tip member 304A to accommodate the small guidewire. Unlike the guidewire guide tube 312A, which may be generally stiffer than the tip member 304A, the clinician may easily deform the tip member 304A to urge the guidewire into the distal lumen 313. Once the guidewire is inserted in the distal lumen 313, the clinician can urge the guidewire proximally past the stepped portion 311 and into the larger guidewire guide tube 312A, which may be positioned within the proximal lumen 315. Furthermore, since most commercial guidewires include a coating (e.g. a hydrophilic or antomicrobial coating, or PTFE coating), the exemplary guide tube and shoulder advantageously avoid damaging or removing the coating. When the wall thickness of the guidewire guide tube 312A is less than the height of the step or shoulder 311, the shoulder 311 may substantially prevent the guidewire guide tube 312A from scraping the exterior coating off of the guidewire. Instead, the guidewire easily passes from the distal lumen 313 to the proximal lumen 315. The guidewire may then be urged proximally through the impeller and catheter assembly until the guidewire protrudes from the proximal end of the system, such as through the proximal guidewire opening 237 described above with reference to FIG. 4.

The guidewire guide features (e.g., guidewire guide tubes 312, 312A) illustrated in FIG. 13-14 include a central lumen passing through the catheter assembly along its length. In some embodiments, it may be desirable to omit the central lumen through the catheter assembly. For example, removing the central lumen from the drive cable and motor assembly may advantageously simplify the manufacturing process and may reduce the profile (e.g., diameter) of the catheter assembly. Accordingly, various embodiments disclosed herein include catheter assemblies that comprise a guidewire guide feature configured to receive a guidewire along a side of the catheter assembly. In some embodiments, the guide feature can be configured to receive a guidewire only along the side of the catheter assembly. In other embodiments, the guide feature can be configured to receive a guidewire along a portion of the side of the catheter assembly and through a central lumen that extends along only a portion of the catheter assembly.

Figure 15:
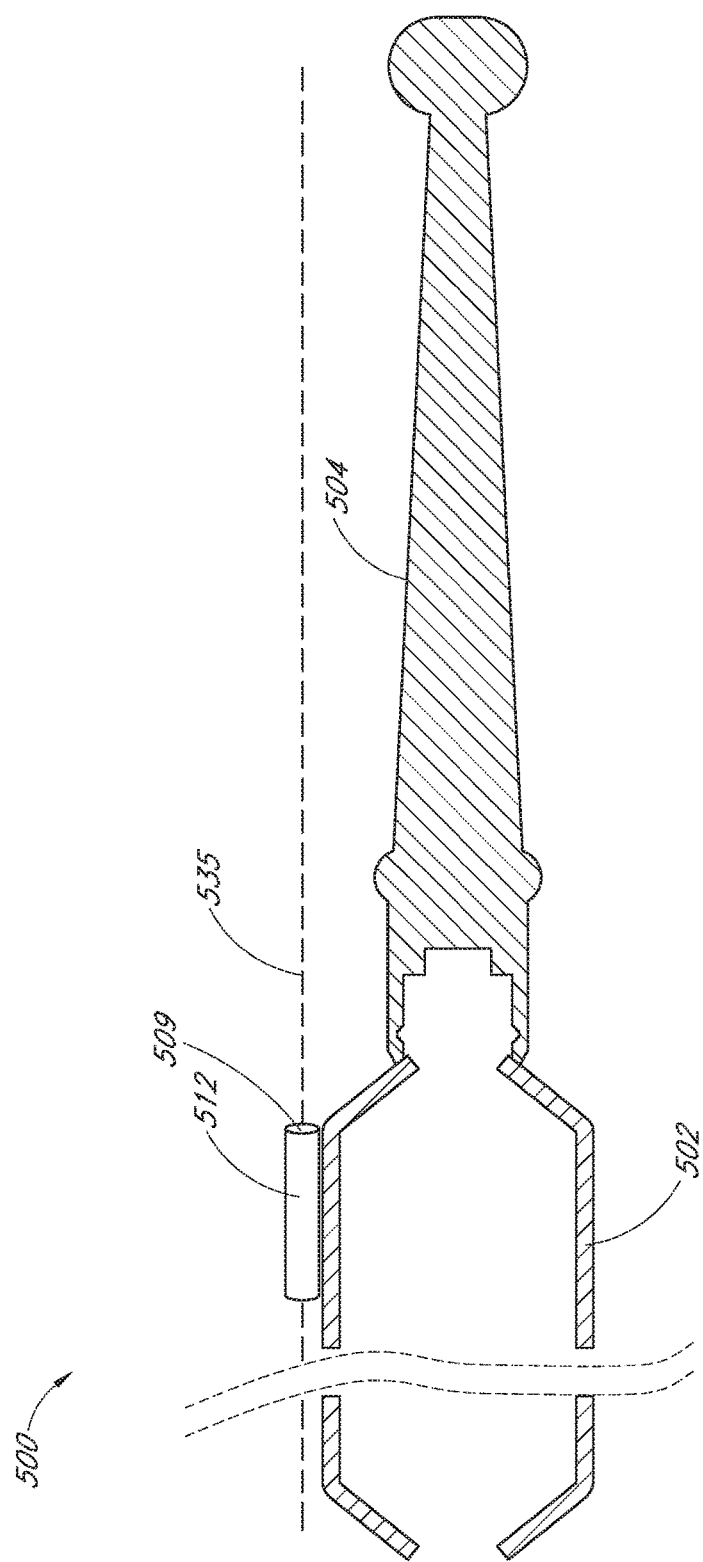
FIG. 15 is a schematic side cross-sectional view of a distal end portion of a catheter assembly having a guide feature along a side of a cannula housing, according to one embodiment.

FIG. 15 is a schematic side cross-sectional view of a distal end portion 500 of a catheter assembly having a guide feature 512 along a side of a cannula housing 502. As with the embodiments of FIGS. 13 and 14, a tip member 504 can be coupled with a distal portion of the cannula housing 502. The impeller is not illustrated in FIG. 15 for ease of illustration, but it should be appreciated that, as in the above-described embodiments, the impeller can be disposed in the cannula housing 502. The cannula housing 502 can be similar to the cannula housing 302 or 302A described above. For example, the impeller can be positioned within the cannula housing 502. When the impeller rotates, blood is pumped through the cannula housing 502 and into the vasculature by way of one or more outlets in the cannula housing 502. The impeller and cannula housing 502 can have a collapsed state, in which the cannula housing 502 is inserted into the patient's vascular system and guided to the heart. The cannula housing 502 can be expanded into an expanded or deployed configuration within the heart, and the impeller (not shown in FIG. 15) can be rotated to pump blood. The impeller can be driven by an impeller shaft connected to a motor. The motor can be positioned within the patient's body or outside the patient's body. The cannula housing 502 illustrated schematically in FIG. 15 is shown in the expanded configuration.

Unlike the embodiments of FIGS. 13 and 14, however, in the arrangement shown in FIG. 15, the guide feature 512 is disposed on an outer surface or side of the catheter assembly, rather than through a central lumen of the catheter assembly. In particular, the guide feature 512 is coupled to or formed with an outer wall of the cannula housing 502. The guide feature 512 can comprise a tubular segment having a guide lumen 509 therethrough. The tubular segment can comprise any suitable cross-section, such as a generally cylindrical cross-section or other suitable profile. As with the guidewire guide tube 312, 312A, a guidewire 535 can be inserted through the guide lumen 509 of the guide feature 512. The guidewire 535 can be advanced through the patient's vascular system to a treatment location in the heart (e.g., the left ventricle). The catheter assembly can be advanced over the guidewire 535 until the tip member 504 and cannula housing 502 are disposed at the treatment location. For example, in some procedures, the cannula housing 502 can straddle the aortic valve, and the distal tip member 504 can be disposed in the left ventricle.

In some embodiments, the guide feature 512 can be sufficiently flexible or collapsible such that, when the cannula housing 502 is collapsed (e.g., by way of an outer sheath), the guide feature 512 can also collapse. For example, the guide feature 512 can be formed from a flexible material, such as a polymer, which can deform when a sheath is advanced over the feature 512. In other arrangements, the sheath can be advanced to bear against the proximal end of the guide feature 512. The clinician can urge the sheath against the proximal end of the guide feature 512 to collapse the housing 502. In still other embodiments, the sheath can include a slot or recess aligned with the guide feature 512. The slot or recess can be sized and shaped to accommodate the guide feature 512 such that when the sheath is advanced over the cannula housing 502, the guide feature 512 is received in the slot or recess. Other suitable ways of collapsing the guide feature 512 may be suitable. In other arrangements, the guide feature 512 may not be collapsible, and the outer sheath may have a diameter large enough to accommodate the cannula housing 502 and the guide feature 512 on the outer wall of the housing 502.

By using the guide feature 512 on an outer wall of the cannula housing 502, the profile (e.g., diameter) of the catheter assembly can be reduced. For example, in such arrangements, there may be no central lumen within the drive shaft, motor assembly, and/or tip member 504. Providing a pump with a smaller cross-section may improve the maneuverability of the catheter assembly and may reduce risks associated with hemolysis and other health risks to the patient. Furthermore, it may be easier for the clinician to insert the guidewire through a short, tubular segment on the outside surface of the catheter assembly, rather than through the length of the catheter assembly.

Figure 16:
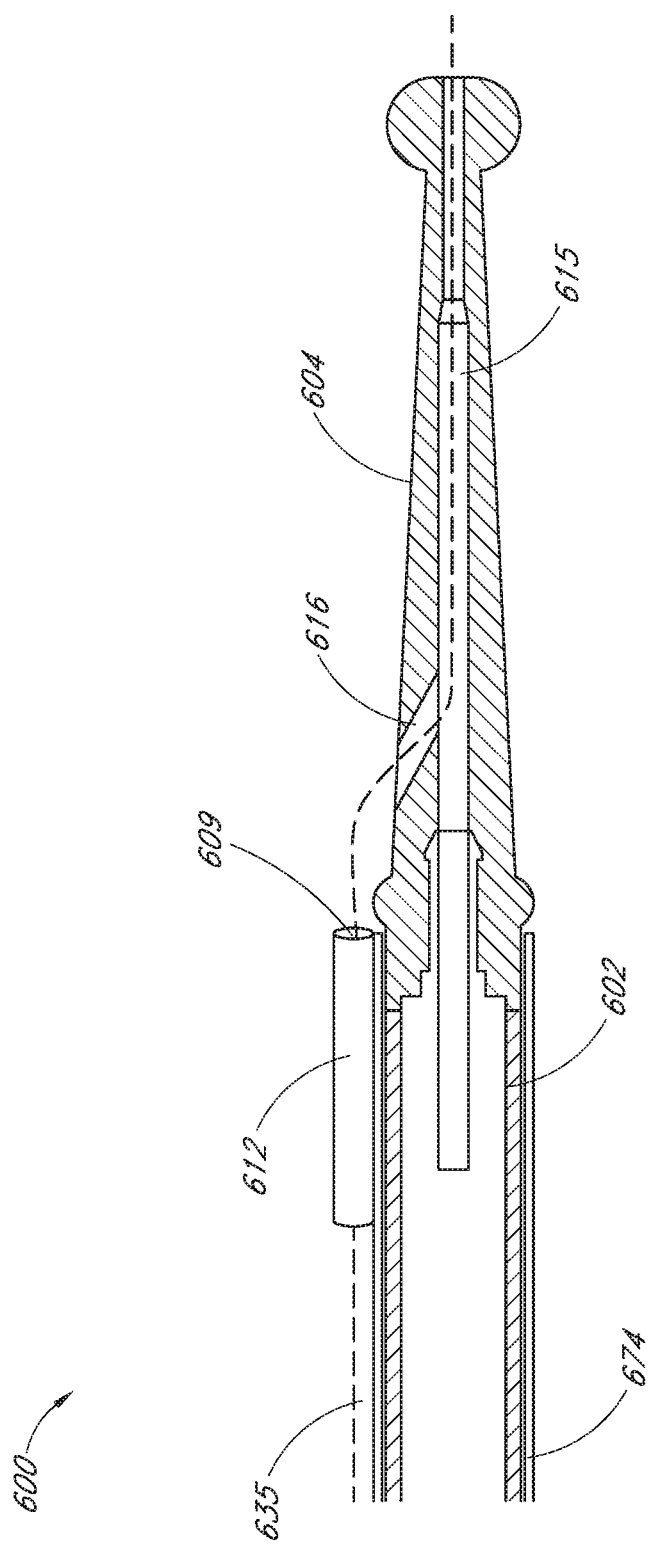
FIG. 16 is a schematic side cross-sectional view of a distal end portion of a catheter assembly having a guide feature along a side of an outer sheath, according to another embodiment.

FIG. 16 is a schematic side cross-sectional view of a distal end portion 600 of a catheter assembly having a guide feature 612 along a side of an outer sheath 674. As with the embodiment of FIG. 15, the catheter assembly can include a cannula housing 602 and a distal tip member 604 coupled with the cannula housing 602. In FIG. 16, the cannula housing 602 is illustrated in the collapsed configuration, e.g., in a stored configuration in which the cannula housing 602 can be percutaneously delivered to the treatment location in the heart. The collapsed cannula housing 602 can be disposed in the outer sheath 674 prior to and during insertion of the catheter assembly into the patient. The cannula housing 602 can be held in the collapsed configuration by the outer sheath 674. When the distal end 600 reaches the treatment location (e.g., the left ventricle), the cannula housing 602 can be urged out of the sheath 674 (or the sheath 674 retracted), and the housing 602 and impeller (not shown in FIG. 16) can expand to the expanded configuration. As with the embodiment of FIG. 15, the impeller can be driven by an impeller shaft connected to a motor. The motor can be positioned within the patient's body or outside the patient's body.

Unlike the embodiment of FIG. 15, however, the guide feature 612 can be disposed on an outer surface or side of the outer sheath 674, rather than on an outer side of the cannula housing 602. In addition, a transition channel 616 can be formed in the tip member 604. The transition channel 616 can extend from an outer surface of the tip member 604 to an internal lumen 615 within the tip member 604. Thus, a proximal end of the transition channel 616 can be open to blood flowing past the tip member 604, and a distal end of the transition channel 616 can connect with the internal lumen 615. The transition channel 616 can enable the use of a rapid exchange guiding system while also allowing the atraumatic tip member 604 to be tracked and controlled during insertion of the catheter assembly. The internal lumen 615 can extend distally through the distal end of the tip member 604. The clinician can insert a guidewire 635 through a guide lumen 609 of the guide feature 612, the transition channel 616, and the internal lumen 615 of the tip member 604. In some embodiments, the clinician can insert the guidewire 635 along a proximal direction, such that the clinician advances the guidewire 635 proximally through the distal end of the tip member 604 and into the internal lumen 615, outwardly through the transition channel 616, and through the guide lumen 609 of the guide feature 612. In such embodiments, for example, the internal lumen 615 may terminate at the connecting channel 616 so that the guidewire is automatically guided through the connecting channel 616 to the outside of the tip member 604. In other embodiments, the clinician can insert the guidewire 635 along a distal direction, such that the clinician inserts the guidewire 635 distally through the lumen 609 of the guide feature 612, inwardly through the transition channel 616, and distally through the internal lumen 615 of the tip member 604 until the guidewire 635 emerges from the distal end of the tip member 604. The clinician can advance the guidewire 635 through the anatomy to the treatment location. The distal portion 600 of the catheter assembly can be urged over the guidewire 635 to position the cannula housing 602 and tip member 604 at the treatment location.

As with the embodiment of FIG. 15, the embodiment illustrated in FIG. 16 may not include a central lumen through proximal portions, such as through the drive shaft and motor assembly. Rather, the internal lumen 615 may be provided through a portion of the catheter assembly, e.g., through at least a portion of the tip member 604. Eliminating the central lumen through the drive shaft and motor assembly may reduce the profile of the catheter assembly and simplify manufacturing techniques. The lumen 615 in the tip member 604 may improve the flexibility of the tip member 604, which may therefore improve the maneuverability of the tip member 604 through the vascular system. Furthermore, providing the guide feature 612 on the outer surface of the outer sheath 674, rather than on the cannula housing 602, may avoid difficulties that may arise when collapsing the cannula housing 502 of FIG. 15. Because the outer sheath 674 is disposed outside the left ventricle during operation of the pump, the guide feature 612 is similarly disposed outside the left ventricle, which may advantageously improve the flow characteristics of blood pumped from the ventricle and may reduce the risk of other complications from disposing the guide feature 612 in the left ventricle during pump operation.

Figure 17A:
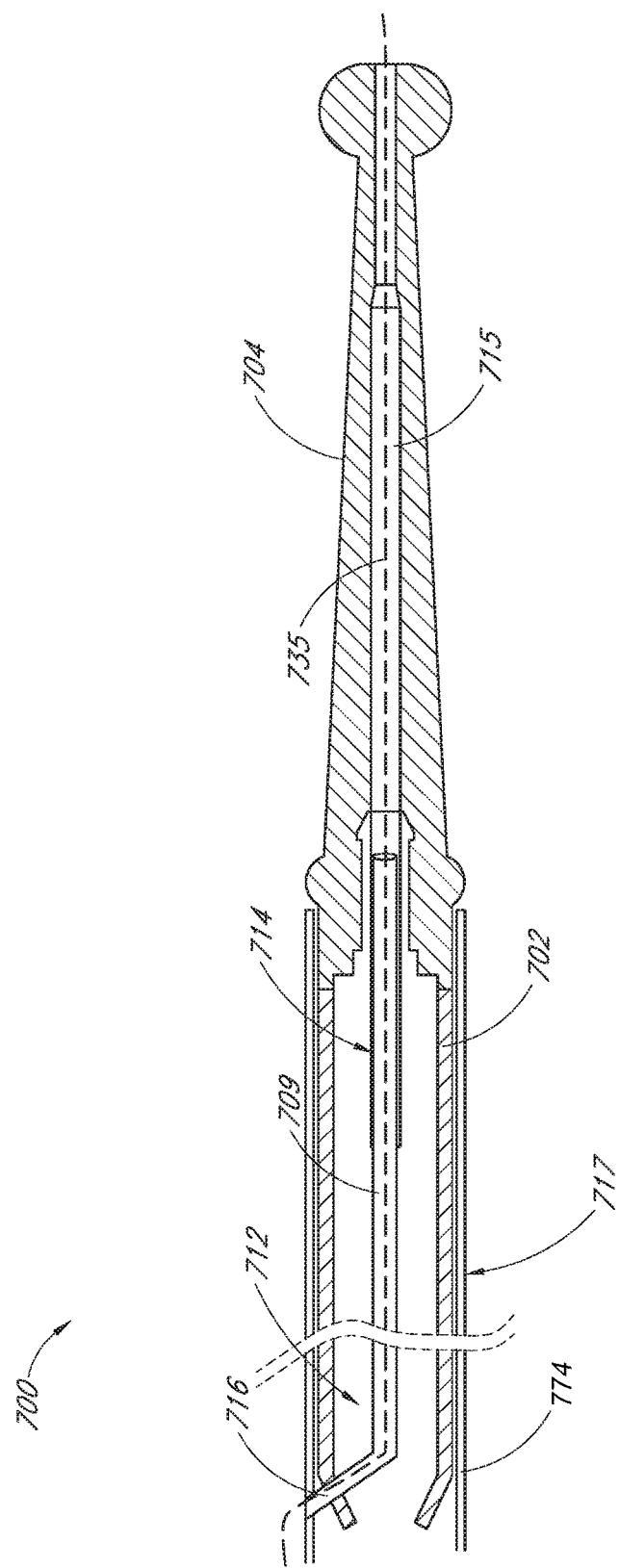
FIG. 17A is a schematic side cross-sectional view of a distal end portion of a catheter assembly having a guide feature extending radially inward from an outer sheath, according to another embodiment.
Figure 17B:
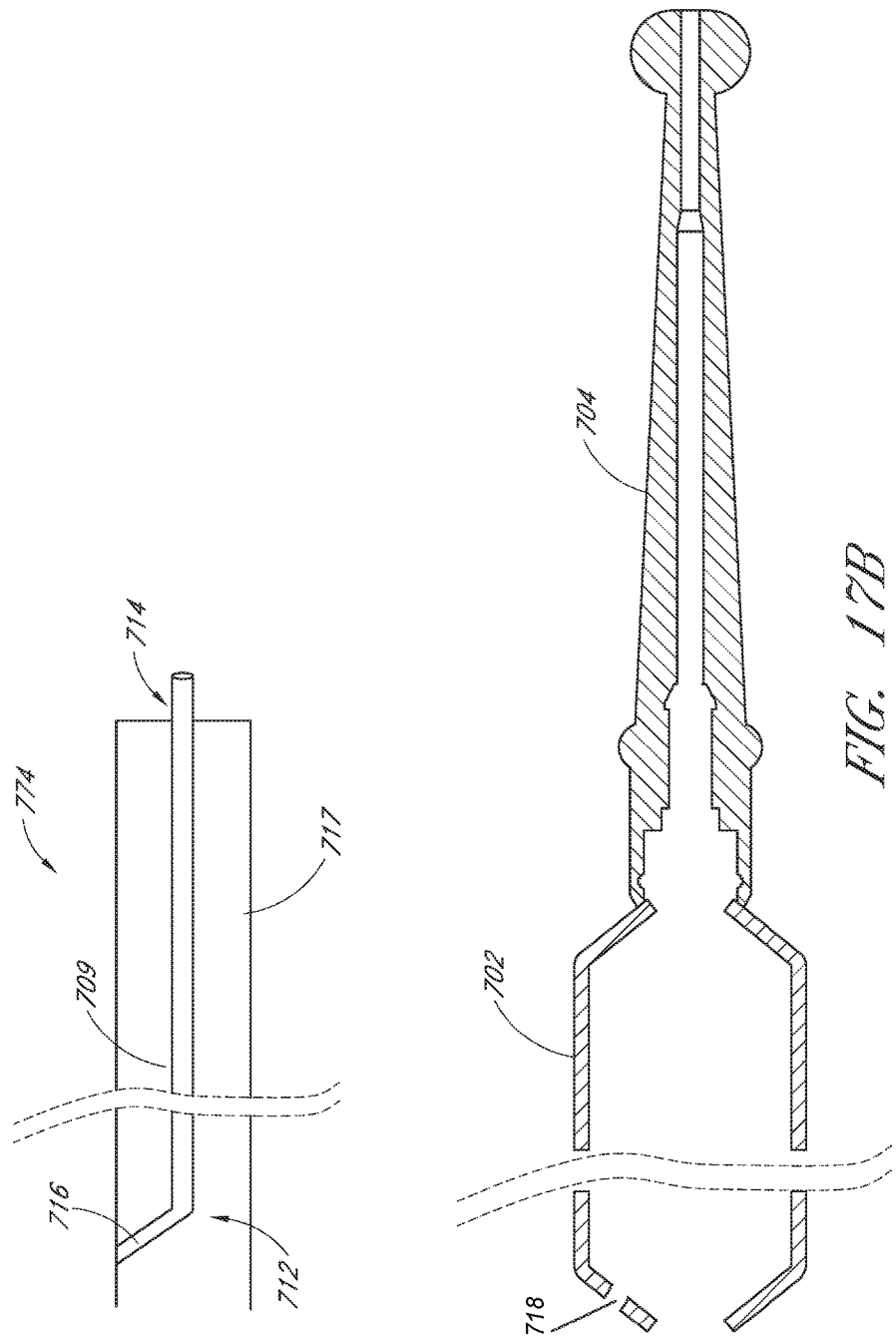
FIG. 17B is a schematic side cross-sectional view illustrating the outer sheath, cannula housing, and tip member in an unassembled configuration, according to the embodiment of FIG. 17A.

FIG. 17A is a schematic side cross-sectional view of a distal end portion 700 of a catheter assembly having a guide feature 712 extending radially inward from an outer sheath 774. FIG. 17B is a schematic side cross-sectional view illustrating the outer sheath 774, cannula housing 702, and tip member 704 in an unassembled configuration. As with the embodiment of FIG. 16, the catheter assembly can include an outer sheath 774, a cannula housing 702 disposed in the outer sheath 774, and a distal tip member 704 coupled with the cannula housing 702. In FIG. 17A, the cannula housing 702 is illustrated in the collapsed configuration; in FIG. 17B, the cannula housing 702 is illustrated in the expanded configuration. As with the embodiment of FIGS. 15-16, the catheter assembly can include an impeller driven by an impeller shaft connected to a motor. The motor can be positioned within the patient's body or outside the patient's body.

Unlike the embodiment of FIG. 16, however, the outer sheath 774 can comprise the guide feature 712, in addition to a tubular wall portion 717 configured to retain the cannula housing 702 and impeller (not shown in FIGS. 17A-17B) in the collapsed or stored configuration. The guide feature 712 can comprise a transition channel 716 extending radially inwardly from the wall portion 717, and an inner portion 714 extending longitudinally within the wall portion 717 (and which may be centered relative to the wall portion 717). A guide lumen 709 of the guide feature 712 can extend through the transition channel 716 and the inner portion 714. As shown in FIG. 17B, the transition channel 716 can be inserted through an aperture 718 in the cannula 702. The aperture 718 can be functionally distinct from one or more outlets on the housing 702. In other arrangements, the transition channel 716 can be inserted through other apertures or windows that form one or more outlets in the catheter assembly.

With reference to FIG. 17A, the clinician can insert a guidewire 735 distally through the transition channel 716 of the sheath 774 and can advance the guidewire 735 through the inner portion 714. A distal end of the inner portion 714 can be disposed at or near the proximal end of the tip member 706 such that the guide lumen 709 communicates with an internal lumen 715 of the tip member 706. The guidewire 735 can be advanced from the inner portion 714 through the internal lumen 715 and out the distal end of the tip member 704. In other arrangements, the guidewire 735 can be advanced proximally such that the guidewire 735 passes proximally through the internal lumen 715, through the inner portion 714, and out through the transition channel 716. As with the embodiments of FIGS. 15 and 16, the clinician can advance the guidewire 735 through the patient's vascular system to the treatment location (e.g., the left ventricle of the heart). The clinician can urge the catheter assembly over the guidewire 735 to position the tip member 704 and cannula housing 702 at the treatment location.

The cannula housing 702 and impeller can be urged from the sheath 774 (or the sheath 774 retracted from the housing 702), and the impeller can be activated to conduct a treatment procedure. When the procedure is complete, in some embodiments, the clinician can advance the sheath 774 over the cannula housing 702 and can align the inner portion 714 of the sheath 774 such that the inner portion 714 is inserted into the aperture 718 of the cannula housing 702. The sheath 774 can collapse the housing 702, and the catheter assembly can be withdrawn from the patient. In other embodiments, the inner portion 714 need not be re-inserted into the aperture 718 because removing the distal end portion 700 from the patient can be done without the use of a guide wire. Accordingly, the inner portion 714 and transition channel 716 may be disposed anywhere inside the sheath 774, e.g., collapsed against an inner wall of the sheath 774 before or while collapsing the cannula housing 702. In still other arrangements, the inner portion 714 and transition channel 716 can be removed prior to collapsing the cannula housing 702.

Advantageously, the embodiment shown in FIGS. 17A-17B can reduce the profile of the catheter assembly by enabling the use of a drive shaft and motor assembly that do not include an inner lumen. Furthermore, as compared with the embodiments of FIGS. 15 and 16, the embodiment of FIGS. 17A-17B do not include a guide feature projecting outward from an outer surface of the assembly, which may enable a decrease in the diameter of the catheter assembly and/or may decrease the difficulty of collapsing the cannula housing in the sheath.

Figure 18:
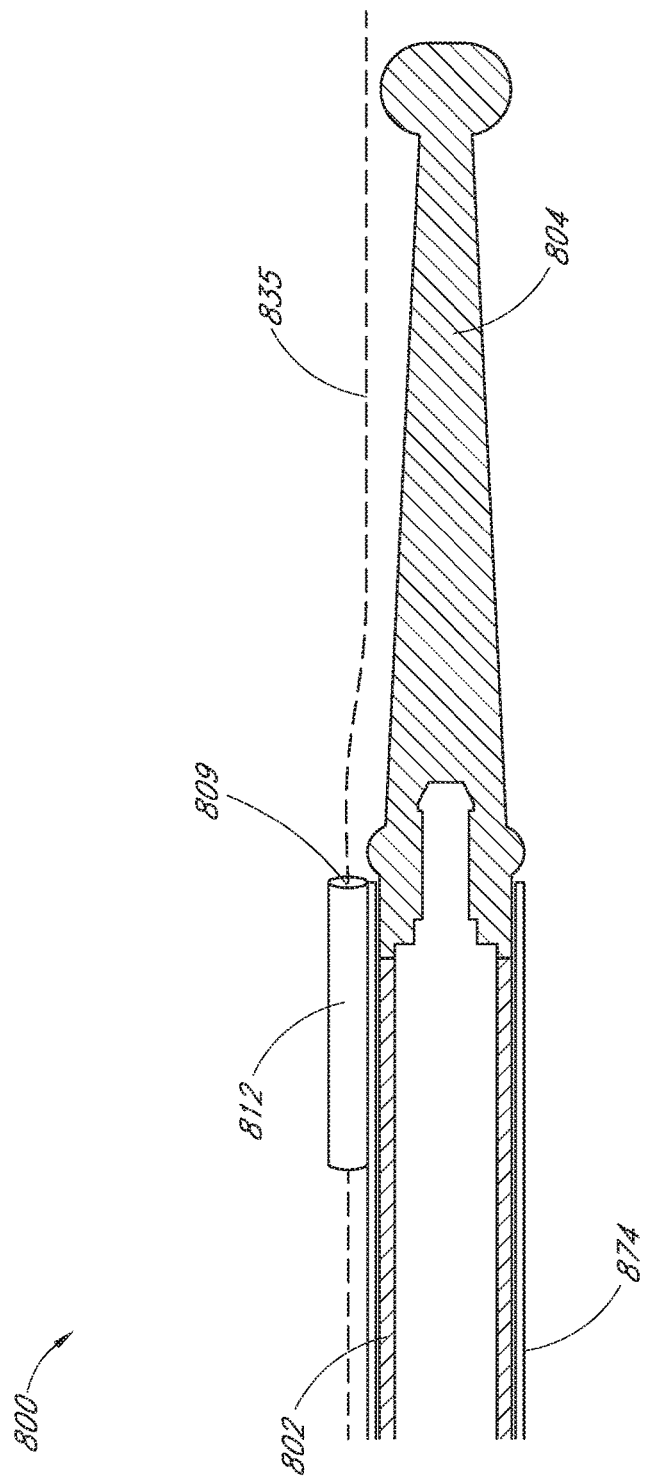
FIG. 18 is a schematic side cross-sectional view of a distal end portion of a catheter assembly having a guide feature along a side of an outer sheath, according to another embodiment.

FIG. 18 is a schematic side cross-sectional view of a distal end portion 800 of a catheter assembly having a guide feature 812 along a side of an outer sheath 874. FIG. 18 is similar to the embodiment shown in FIG. 16, except that a guidewire 835 is advanced only along an outer surface or side of the catheter assembly instead of through a lumen in a tip member 804. For example, as with the embodiment of FIG. 16, a cannula housing 802 (shown in the collapsed configuration) can be retained within a sheath 874, and the tip member 804 can be coupled to a distal portion of the cannula housing 802. As with the embodiments of FIGS. 15-17B, an impeller (not shown) can be driven by an impeller shaft connected to a motor. The motor can be positioned within the patient's body or outside the patient's body.

Moreover, as with the embodiment of FIG. 16, a guide feature 812 (which may comprise a short tubular segment) can be coupled to an outer surface of the sheath 874. Unlike the embodiment of FIG. 16, however, the tip member 804 does not include a transition channel through which a guidewire is passed. In the embodiment of FIG. 18, the tip member 804 may not include an inner lumen. Instead, the clinician can insert the guidewire 835 through a guide lumen 809 of the guide feature 812 and can pass the guidewire 835 along the outside of the tip member 804. As with the above embodiments, the clinician can advance the guidewire 835 through the patient's vasculature to the treatment location. The catheter assembly can be urged along the guidewire 835 to the treatment location. Advantageously, the embodiment of FIG. 18 can reduce the profile of the catheter assembly. Furthermore, because there may be no inner lumen within the tip member 804, the embodiment of FIG. 18 may prevent blood from collecting in the tip member 804.

Figure 19:
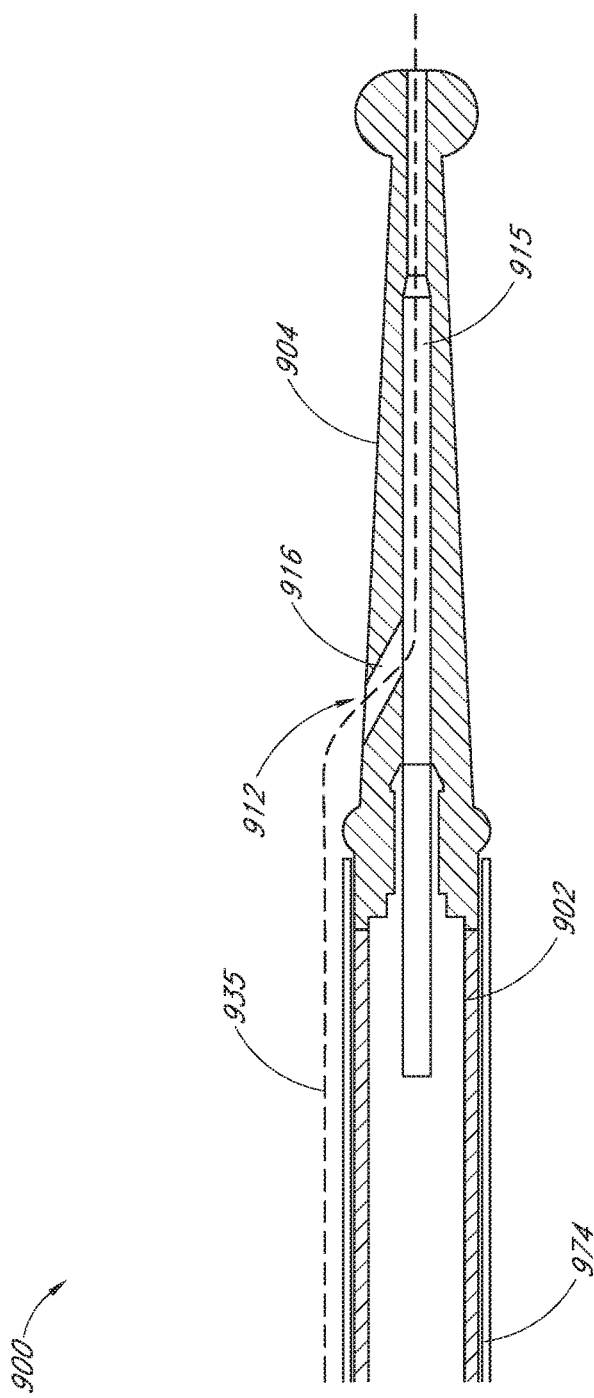
FIG. 19 is a schematic side cross-sectional view of a distal end portion of a catheter assembly having a guide feature extending through a tip member.

FIG. 19 is a schematic side cross-sectional view of a distal end portion 900 of a catheter assembly having a guide feature 912 extending through a tip member 904. The embodiment shown in FIG. 19 is similar to the embodiment of FIG. 16, except the guide feature 912 is disposed entirely within the tip member 904, instead of including a portion along the outside of an outer sheath 974. For example, as with FIG. 16, a cannula housing 902 can be retained within the sheath 974. As with the embodiment of FIGS. 15-18, an impeller (not shown) can be driven by an impeller shaft connected to a motor. The motor can be positioned within the patient's body or outside the patient's body. Unlike FIG. 16, however, the embodiment of FIG. 19 does not include a tubular segment on the outside of the sheath 974. Rather, the guide feature 912 includes a transition channel 916 and internal lumen 915 formed through the tip member 904. The clinician can insert a guidewire 935 through the transition channel 916 and can advance the guidewire through the internal lumen 915. The guidewire 935 can be inserted into the patient's anatomy, and the catheter assembly can be urged over the guidewire 935 to the treatment location. The embodiment of FIG. 19 can advantageously be used without guide features on the outside of the catheter assembly (such as the guide feature 612 of FIG. 16). Furthermore, although the tip member 904 can include internal lumen 915 and channel 916, there may be no inner lumen formed in the drive shaft or motor assembly, which can reduce the profile of the catheter assembly. Furthermore, in some embodiments, the internal lumen 915 can terminate at or near the transition channel 916 such that the guidewire is automatically directed or guided through the transition channel 916 and outside the tip member 904.

Figure 20:
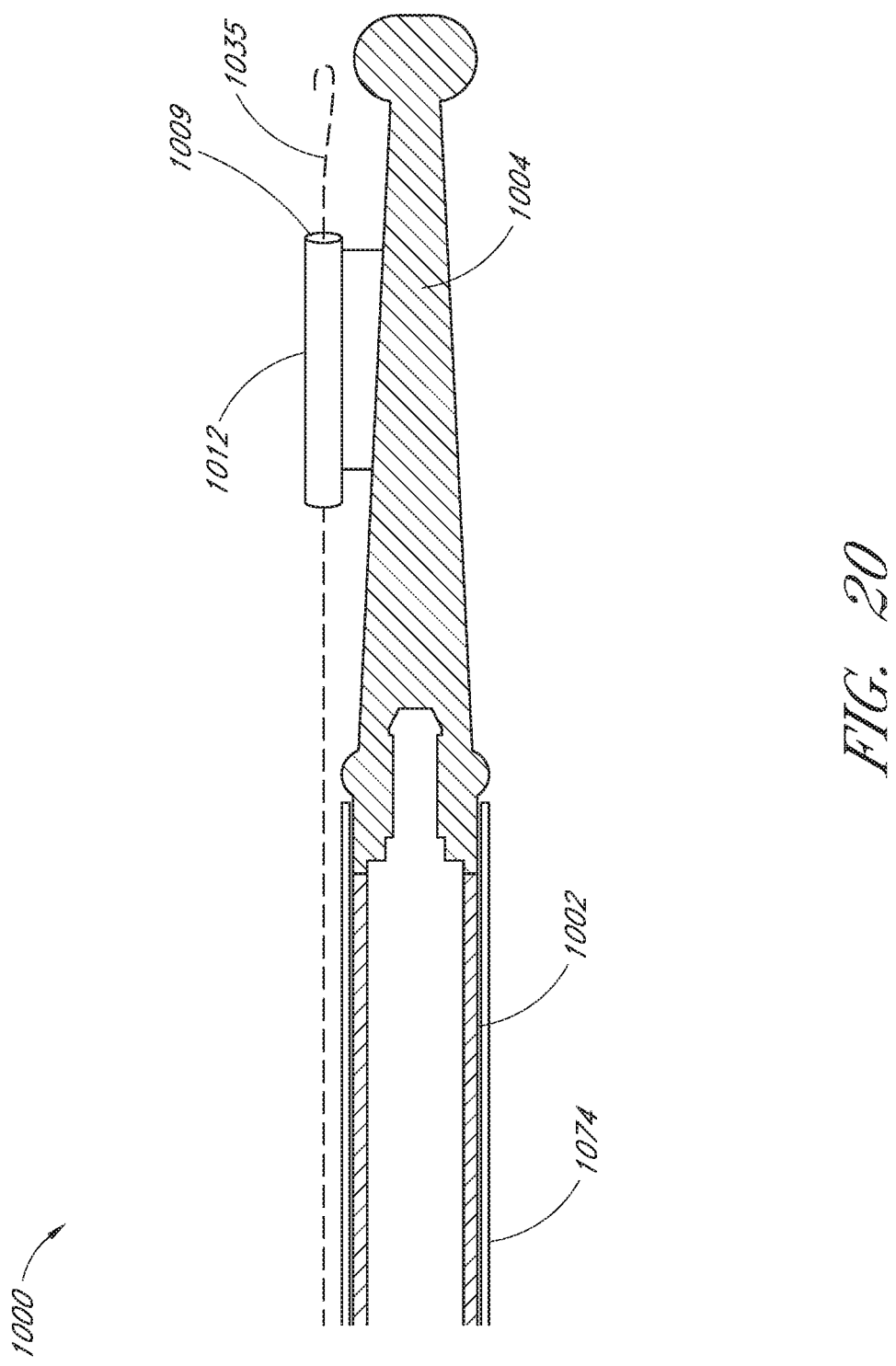
FIG. 20 is a schematic side cross-sectional view of a distal end portion of a catheter assembly having a guide feature disposed on an outer surface of a tip member, according to another embodiment.

FIG. 20 is a schematic side cross-sectional view of a distal end portion 1000 of a catheter assembly having a guide feature 1012 (not shown in cross-section) disposed on an outer surface of a tip member 1004. The distal end portion 1000 can include an outer sheath 1074 and a cannula housing 1002 retained within the sheath 1074. The tip member 1004 can be coupled with the cannula housing 1002. A guide feature 1012 (e.g., a short tubular segment) can be coupled with an outer surface of the tip member 1004. The guide feature 1012 can include a guide lumen 1009 through which a guidewire 1035 can be inserted. As with the above embodiments, the clinician can advance the guidewire 1035 through the vascular system of the patient, and can urge the distal end portion 1000 of the catheter assembly over the guidewire 1035 to the treatment location. Advantageously, the embodiment of FIG. 20 can reduce the profile of the catheter assembly be omitting an internal lumen within the catheter assembly. Furthermore, by disposing the guide feature 1012 on the tip member 1004, rather than on the cannula housing 1002, the sheathing and collapse of the cannula housing 1002 may not be affected by the guide feature 1012.

The guide feature 1012 in FIG. 20 is illustrated at an intermediate portion of the tip member 1004. In other embodiments, however, the guide feature 1012 may be positioned nearer a proximal portion of the tip member 1004, e.g., near the housing 1002. In other arrangements, the guide feature 1012 may be positioned nearer a distal portion of the tip member 1004, e.g., near the atraumatic ball-like tip. The tip member 1004 and guide feature 1012 may be configured to have a low profile, which can assist with insertion of the catheter assembly into the patient's body. For example, the guide feature 1012 can be connected with the tip member 1004 such that the combined width of the guide feature 1012 and tip member 1004 is as small as possible. A low profile arrangement may also be enabled at least in part by not providing a central or internal lumen, such as the lumen 915 shown in FIG. 19. As with the embodiments of FIGS. 15-19, an impeller (not shown) can be driven by an impeller shaft connected to a motor. The motor can be positioned within the patient's body or outside the patient's body.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter assembly comprising:
    a cannula disposed at a distal portion of the catheter assembly, the cannula having a collapsed configuration and an expanded configuration, the cannula arranged to permit the flow of blood therethrough when in the expanded configuration;
    a tip member coupled with a distal portion of the cannula; and
    a guide feature configured to receive a guidewire through a guide lumen formed through the guide feature,
    wherein the catheter assembly is configured such that, when the catheter assembly is inserted into a patient with the guidewire, the guidewire passes through the guide lumen and extends longitudinally along at least a portion of an outer surface of a side of the catheter assembly.

2. The catheter assembly of claim 1, wherein the guide feature comprises a tubular segment coupled to an outer surface of the cannula.

3. The catheter assembly of claim 1, wherein the guide feature comprises a tubular segment coupled to an outer surface of the tip member.

4. The catheter assembly of claim 1, further comprising a retainer sheath to retain the cannula in the collapsed configuration for insertion and removal from the patient.

5. The catheter assembly of claim 4, wherein the guide feature comprises a tubular segment coupled to an outer surface of the retainer sheath.

6. The catheter assembly of claim 5, wherein the tip member comprises an internal lumen therethrough and a transition channel extending from the internal lumen to an outer surface of the tip member, wherein the guide lumen of the guide feature extends through the tubular segment, the transition channel, and the internal lumen of the tip member.

7. The catheter assembly of claim 4, wherein the retainer sheath comprises a tubular wall, a transition channel extending radially inward from the tubular wall, and an inner portion extending longitudinally from the transition channel, the guide lumen comprising the transition channel and the inner portion.

8. The catheter assembly of claim 7, wherein the cannula comprises an aperture formed through a wall of the cannula, the aperture arranged to receive the inner portion of the retainer sheath when the retainer sheath is urged over the cannula to collapse the cannula.

9. The catheter assembly of claim 1, wherein the tip member comprises an internal lumen therethrough and a transition channel extending from the internal lumen to an outer surface of the tip member, and wherein the guide lumen extends through the transition channel and the internal lumen of the tip member.

10. A catheter assembly comprising:
an expandable cannula disposed at a distal portion of the catheter assembly, the expandable cannula having a collapsed configuration and an expanded configuration, the expandable cannula arranged to permit the flow of blood therethrough when in the expanded configuration; and
a guide feature having a guide lumen extending distally of a proximal end of the guide feature, the proximal end of the guide feature located adjacent to or distal of the proximal end of the expandable cannula, the guide lumen configured to pass a guide wire therethrough.

11. The catheter assembly of claim 10, further comprising a tip member coupled with a distal portion of the expandable cannula.

12. The catheter assembly of claim 11, wherein the guide feature includes a portion disposed in the tip member.

13. The catheter assembly of claim 10, wherein the guide feature includes a portion disposed through the expandable cannula.

14. The catheter assembly of claim 10, wherein the guide feature is disposed outward of an outer surface of the expandable cannula.

15. The catheter assembly of claim 14 further comprising a sheath, wherein at least a portion of the guide feature is disposed on the sheath.

16. The catheter assembly of claim 10 further comprising a motor, wherein the catheter assembly includes an elongate body having a proximal end and a distal end, the motor being disposed adjacent to the distal end of the elongate body and adjacent to the proximal end of the expandable cannula.

* * * * *